US012656683B2

(12) United States Patent
Sasami et al.

(10) Patent No.: US 12,656,683 B2
(45) Date of Patent: Jun. 16, 2026

(54) RESIST COMPOSITION AND PATTERNING PROCESS

(71) Applicant: SHIN-ETSU CHEMICAL CO., LTD., Tokyo (JP)

(72) Inventors: Takeshi Sasami, Joetsu (JP); Masayoshi Sagehashi, Joetsu (JP); Kenji Yamada, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 523 days.

(21) Appl. No.: 18/126,098

(22) Filed: Mar. 24, 2023

(65) Prior Publication Data

US 2023/0305398 A1 Sep. 28, 2023

(30) Foreign Application Priority Data

Mar. 28, 2022 (JP) ................................ 2022-052470

(51) Int. Cl.

| | |
|---|---|
| ***G03F 7/039*** | (2006.01) |
| ***C07C 381/12*** | (2006.01) |
| ***C08F 220/18*** | (2006.01) |
| ***C08F 220/22*** | (2006.01) |

(52) U.S. Cl.

CPC ............ *G03F 7/039* (2013.01); *C07C 381/12* (2013.01); *C08F 220/1805* (2020.02); *C08F 220/1806* (2020.02); *C08F 220/1807* (2020.02); *C08F 220/1808* (2020.02); *C08F 220/1809* (2020.02); *C08F 220/22* (2013.01); *G03F 7/0392* (2013.01)

(58) Field of Classification Search

CPC ................ G03F 7/0392; C08F 220/282; C08F 220/304; C08F 220/38; C08F 220/32;

(Continued)

(56) References Cited

U.S. PATENT DOCUMENTS 8,614,046 B2 * 12/2013 Ichikawa .............. G03F 7/0045 430/326

8,900,792 B2 * 12/2014 Thackeray ........... C07D 333/76 430/326

(Continued)

FOREIGN PATENT DOCUMENTS

JP H04-230645 A 8/1992

JP 2008-111103 A 5/2008

(Continued)

OTHER PUBLICATIONS

Dec. 6, 2023 Office Action issued in Taiwanese Patent Application No. 112111607.

(Continued)

*Primary Examiner* — Amanda C. Walke

(74) *Attorney, Agent, or Firm* — Oliff PLC

(57) ABSTRACT

The present invention is a resist composition, including: a resin (A) having: a repeating unit represented by the general formula (p-1); a repeating unit represented by the general formula (a-1); and a repeating unit represented by the general formula (b-1); a resin (B) having: a repeating unit represented by the general formula (p-2); a repeating unit represented by the general formula (a-1); and a repeating unit represented by the general formula (b-1); and a solvent (D), wherein a content of the resin (A) contained in the resist composition is smaller than a content of the resin (B). This provides a resist composition that reduces roughness and size uniformity of a hole pattern with high resolution exceeding that of conventional resist materials even with a high exposure-dose region, that has good pattern shape after exposure, and that has excellent etching resistance.

(p-1)

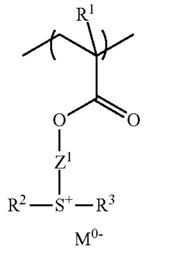

(p-2)

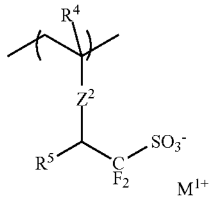

(a-1)

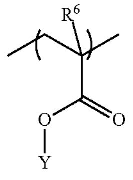

(b-1)

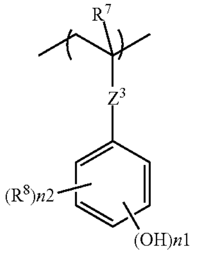

15 Claims, No Drawings

(58) Field of Classification Search
CPC .............. C08F 220/303; C08F 220/302; C08F 220/301; C08F 220/30; C07C 381/12
See application file for complete search history.

(56) References Cited

U.S. PATENT DOCUMENTS

| | | | | |
|---|---|---|---|---|
| 9,354,515 | B2 * | 5/2016 | Nagamine | G03F 7/0046 |
| 9,766,547 | B2 | 9/2017 | Takizawa et al. | |
| 10,781,276 | B2 * | 9/2020 | Enomoto | G03F 7/0045 |
| 11,609,497 | B2 * | 3/2023 | Sasami | C08F 212/32 |
| 2008/0090172 | A1 | 4/2008 | Hatakeyama et al. | |
| 2008/0118860 | A1 | 5/2008 | Harada et al. | |
| 2009/0081588 | A1 | 3/2009 | Hatakeyama et al. | |
| 2009/0111047 | A1 | 4/2009 | Yamashita | |
| 2009/0208867 | A1 | 8/2009 | Harada et al. | |
| 2009/0208873 | A1 | 8/2009 | Harada et al. | |
| 2009/0269696 | A1 | 10/2009 | Ohsawa et al. | |
| 2009/0280434 | A1 | 11/2009 | Harada et al. | |
| 2010/0112482 | A1 | 5/2010 | Watanabe et al. | |
| 2010/0136482 | A1 | 6/2010 | Harada et al. | |
| 2010/0209827 | A1 | 8/2010 | Ohashi et al. | |
| 2010/0266957 | A1 | 10/2010 | Harada et al. | |
| 2011/0008735 | A1 | 1/2011 | Ohsawa et al. | |
| 2012/0009527 | A1 * | 1/2012 | Hatakeyama | G03F 7/2041 430/325 |
| 2012/0164577 | A1 | 6/2012 | Taniguchi et al. | |
| 2012/0214100 | A1 * | 8/2012 | Kobayashi | G03F 7/0045 430/285.1 |
| 2013/0108960 | A1 * | 5/2013 | Hatakeyama | G03F 7/0395 430/296 |
| 2013/0230804 | A1 * | 9/2013 | Sakakibara | C07C 381/12 430/281.1 |
| 2014/0017617 | A1 * | 1/2014 | Arai | C08F 220/24 560/222 |
| 2015/0086926 | A1 | 3/2015 | Ohashi et al. | |
| 2015/0268552 | A1 * | 9/2015 | Nam | G03F 1/26 430/5 |
| 2016/0103392 | A1 * | 4/2016 | LaBeaume | C07C 309/12 430/311 |
| 2020/0133121 | A1 | 4/2020 | Domon et al. | |
| 2021/0188770 | A1 | 6/2021 | Fujiwara et al. | |
| 2022/0050378 | A1 | 2/2022 | Hatakeyama et al. | |
| 2022/0260908 | A9 * | 8/2022 | Kaneko | G03F 7/0384 |

FOREIGN PATENT DOCUMENTS

| | | | | |
|---|---|---|---|---|
| JP | 2008-122932 | A | 5/2008 | |
| JP | 2009-098638 | A | 5/2009 | |
| JP | 2009-109595 | A | 5/2009 | |
| JP | 2009-191151 | A | 8/2009 | |
| JP | 2009-192784 | A | 8/2009 | |
| JP | 2009-263487 | A | 11/2009 | |
| JP | 2009-276363 | A | 11/2009 | |
| JP | 2010-107695 | A | 5/2010 | |
| JP | 2010-134012 | A | 6/2010 | |
| JP | 2010-215608 | A | 9/2010 | |
| JP | 2010-250105 | A | 11/2010 | |
| JP | 2011-016746 | A | 1/2011 | |
| JP | 2011-042789 | A | 3/2011 | |
| JP | 2012-046501 | A | 3/2012 | |
| JP | 2012-137518 | A | 7/2012 | |
| JP | 2015-043067 | A | 3/2015 | |
| JP | 2015-054833 | A | 3/2015 | |
| JP | 2015-168712 | A | 9/2015 | |
| TW | 202024031 | A | 7/2020 | |
| TW | 202128602 | A | 8/2021 | |
| TW | 202210948 | A | 3/2022 | |
| WO | WO-2013024756 | A1 * | 2/2013 | G03F 7/0045 |

OTHER PUBLICATIONS

Feb. 3, 2026 Office Action issued in Japanese Patent Application No. 2023-044648.

* cited by examiner

RESIST COMPOSITION AND PATTERNING PROCESS

TECHNICAL FIELD

The present invention relates to a resist composition and a patterning process using the resist composition.

BACKGROUND ART

As higher integration and higher speed of LSI have been achieved, the pattern rule has been rapidly miniaturized. In particular, expansion of the flash memory market and increase in a memory capacity is leading the miniaturization. As the latest miniaturization technology, devices with a 65-nm node are industrially produced by ArF lithography, and industrial production of devices with a 45-nm node by ArF immersion lithography, which is the next generation, is being prepared. Prospects for a 32-nm node, which is the next generation, include: an immersion lithography with an ultrahigh NA lens combining a liquid having higher refractive index than water, a high refractive-index lens, and a high refractive-index material; extreme ultraviolet (EUV) lithography with a wavelength of 13.5 nm; and double exposure (double patterning lithography) of the ArF lithography. The investigation is underway.

To improve resolution and size controllability with the high-energy ray, a resist film tends to have lower sensitivity. The decrease in the sensitivity of the resist film lowers the productivity, which is unfavorable. For a demand of higher sensitivity, a chemically amplified resist material is investigated.

As the miniaturization advances, edge roughness of a line pattern (line edge roughness: LER and line width roughness: LWR) and size uniformity of a hole pattern (critical dimension uniformity: CDU) have become a problem. Pointed out are an effect of dissolution contrast of a base polymer in a developer, an effect of uneven distribution and aggregation of an acid generator, and an effect of acid diffusion. In addition, the LER tends to be higher as the resist film has a smaller thickness, and deterioration in LER and etching resistance due to the thinning with the miniaturization advance becomes considerable problems.

Patent Document 1 discloses that introducing a photoacid generator into a base polymer as an anion monomer inhibits the acid diffusion and yields excellent resolution in a positive-type, fine line pattern formation.

Patent Document 2 discloses that introducing a photoacid generator into a polymer as a cation fails to inhibit the acid diffusion and it is difficult to improve the LER.

Patent Document 3 discloses that combination of: a polymer compound having a photoacid generator to generate an alkanesulfonic acid substituted with a fluorine atom at the α-position; and an acid generator to generate an alkanesulfonic acid not substituted with a fluorine atom at the α-position of the sulfonic acid improves a depth of focus, circularity, and LWR of a hole pattern or a trench pattern. This effect is derived from the alkanesulfonic acid substituted with a fluorine atom at the α-position having higher acid strength than the alkanesulfonic acid not substituted with a fluorine atom.

It is presumed that, in these prior art, the strong acid generated from the photoacid generator by exposure is salt-exchanged with the weak acid onium salt for forming a strong acid onium salt to substitute the strong acid having high acidity with the weak acid, and an acid generation and decomposition reaction of an acid-labile group is inhibited to shorten a distance of the acid diffusion. That is, the weak acid onium salt is considered to function as a quencher (acid deactivator) against the strong acid generated by exposure. Since being typically non-volatile compared with a nitrogen-containing compound such as amines, the weak acid onium salt can prevent a change in concentration in a resist film surface layer during the resist film formation and a baking process in the patterning, and forms a better rectangular pattern.

Patent Document 4 discloses that using an alkanesulfonate onium has insufficiently lower acidity than a carboxylate onium salt, and thereby has a lower quenching ability, leading to unsatisfactory resolution, edge roughness, and depth of focus.

From the viewpoint of a trade-off between sensitivity and resolution, pattern formation with high exposure-dose region may be desired to have higher resolution and reduced LER and CDU. Such a polymer into which the anion monomer is introduced generates a larger amount of a decomposed product of the photoacid generator, and the generated anion unintentionally increases solubility of the base polymer in an alkaline developer compared with a base polymer having no photo-decomposable group. When the solubility of the anion portion of the polymer in the alkaline developer due to the exposure differs from solubility with elimination of the acid-labile group, the dissolution contrast is problematically decreased. In addition, when an addition amount of an acid diffusion inhibitor increases to inhibit the acid diffusion, the solubility of the resist film in an alkaline developer increases, leading to decrease in the dissolution contrast.

CITATION LIST

Patent Literature

Patent Document 1: JP 2009-263487 A
Patent Document 2: JP H04-230645 A
Patent Document 3: JP 2012-137518 A
Patent Document 4: JP 2015-054833 A

SUMMARY OF INVENTION

Technical Problem

The present invention has been made in view of the above circumstances. An object of the present invention to provide a resist composition that reduces roughness (LER and LWR) and size uniformity (CDU) of a hole pattern with high resolution exceeding that of conventional resist materials even with a high exposure-dose region, that has good pattern shape after the exposure, and that has excellent etching resistance.

Solution to Problem

To solve the above problem, the present invention provides a resist composition, comprising:

- a resin (A) having: a repeating unit represented by the following general formula (p-1); a repeating unit represented by the following general formula (a-1) and changing in its polarity by an action of an acid to be soluble in an alkaline aqueous solution; and a repeating unit represented by the following general formula (b-1);
- a resin (B) having: a repeating unit represented by the following general formula (p-2); a repeating unit represented by the following general formula (a-1) and changing in its polarity by an action of an acid to be soluble in an alkaline aqueous solution; and a repeating unit represented by the following general formula (b-1); and a solvent (D), wherein a content of the resin (A) contained in the resist composition is smaller than a content of the resin (B), (p-1)

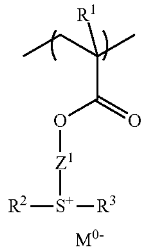

(p-2)

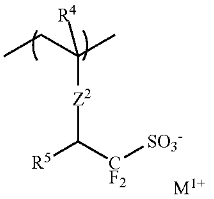

(a-1)

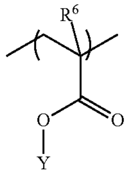

(b-1)

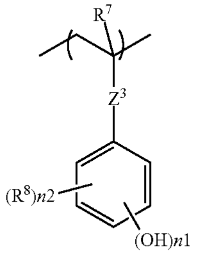

wherein in the general formula (p-1), $R^1$ represents a hydrogen atom or a methyl group;

$Z^1$ represents a single bond, a phenylene group, —O—$Z^{11}$—, —C(═O)—O—$Z^{11}$—, —C(═O)—NH—$Z^{11}$—, —$Z^{12}$-Ph-, —$Z^{12}$—O-Ph-, or —$Z^{12}$—C(═O)—O-Ph-; $Z^{11}$ represents an alkanediyl group having 1 to 6 carbon atoms, an alkenediyl group having 2 to 6 carbon atoms, or a phenylene group, $Z^{11}$ optionally having a carbonyl group, an ester bond, an ether bond, or a hydroxy group; $Z^{12}$ represents a hydrocarbon group having 1 to 15 carbon atoms; Ph represents a phenylene group;

$R^2$ and $R^3$ each independently represents a monovalent hydrocarbon group having 1 to 20 carbon atoms and optionally having a heteroatom, or a phenyl group;

$M^{0-}$ represents a non-nucleophilic counterion;

in the general formula (p-2), $R^4$ represents a hydrogen atom or a methyl group;

$Z^2$ represents a single bond, a phenylene group, —O—$Z^{21}$—, —C(═O)—O—$Z^{21}$—, —$Z^{21}$—C(═O)—O—, or —C(═O)—NH—$Z^{21}$—; $Z^{21}$ represents a single bond, an alkanediyl group having 1 to 20 carbon atoms, an alkenediyl group having 2 to 20 carbon atoms, or a phenylene group, $Z^{21}$ optionally having a carbonyl group, an ester bond, an ether bond, or a hydroxy group;

$M^{1+}$ represents a counter cation having a substituent and being a sulfonium cation, an iodonium cation, or an ammonium cation;

$R^5$ represents a hydrogen atom or a trifluoromethyl group;

in the general formula (a-1), $R^6$ represents a hydrogen atom or a methyl group;

Y represents a group having a structure changing in its polarity by an action of an acid to be soluble in an alkaline aqueous solution;

in the general formula (b-1), $R^7$ represents a hydrogen atom or a methyl group;

$Z^3$ represents a single bond, a methylene group, an ethylene group, a phenylene group, a fluorinated phenylene group, an ester bond, an amide bond, —O—$Z^{31}$—, —C(═O)—O—$Z^{31}$—, or —C(═O)—NH—$Z^{31}$—; $Z^{31}$ represents an alkanediyl group having 1 to 12 carbon atoms and optionally having a carbonyl group, an ester bond, or an ether bond;

"n1" represents an integer of 1 to 3; "n2" represents an integer of 0 to 3; a total of "n1" and "n2" is 5 or less; and $R^8$ represents a halogen atom, a linear hydrocarbon group having 1 to 10 carbon atoms, or a branched or cyclic hydrocarbon group having 3 to 10 carbon atoms, and —$CH_2$-constituting these groups are optionally substituted with —O—, —C(═O)—O—, or —C(═O)—, or optionally substituted with a hydrogen atom, a halogen atom, or a heteroatom.

Such a resist composition can form a rigid film by forming a polymer composite having a large apparent molecular weight with an ionic interaction between the polymers of the anion-introduced base polymer and the cation-introduced base polymer. Thus, the resist composition can provide a resist film having reduced solubility in an alkaline developer even in a high exposure-dose region, having reduced edge roughness (LER and LWR) and size uniformity (CDU) of a hole pattern with high resolution, having good pattern shape after the exposure, and having excellent etching resistance.

In the inventive resist composition, the non-nucleophilic counterion $M^{0-}$ in the general formula (p-1) is preferably represented by the following general formula (e-0), (e-0)

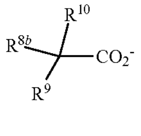

wherein $R^{8b}$ and $R^9$ each independently represent a hydrogen atom, a fluorine atom, or a trifluoromethyl group; and $R^{10}$ represents a hydrogen atom, a hydroxy group, a substituted or unsubstituted linear alkyl group having 1 to 20 carbon atoms, a substituted or unsubstituted branched or cyclic alkyl group having 3 to 20 carbon atoms, or a substituted or unsubstituted aryl group having 6 to 30 carbon atoms.

Such a resist composition can provide a resist composition having excellent rectangular formability of the pattern after development and excellent edge roughness.

In the inventive resist composition, the resin (A) and the resin (B) preferably have no repeating unit having a lactone structure.

Such a resist composition can inhibit permeating the alkali developer into the pattern to inhibit swelling, and yield a resist pattern having further preferable shape.

The inventive resist composition preferably further comprises a resin (C) having no repeating unit changing in its polarity by an action of an acid to be soluble in an alkaline aqueous solution.

Such a resist composition can improve uniformity of a film thickness of the resist film on the wafer surface applied by spin-coating.

The resin (C) preferably has a repeating unit represented by the following general formula (c-1), (c-1)

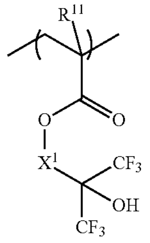

wherein $R^{11}$ represents a hydrogen atom or a methyl group;

$X^1$ represents a single bond or a divalent linking group selected from a divalent hydrocarbon group having 1 to 10 carbon atoms, a fluorinated phenylene group, $—O—X^{11}—$, $—C(=O)—O—X^{11}—$, and $—C(=O)—NH—X^{11}—$; and $X^{11}$ represents an alkanediyl group having 1 to 20 carbon atoms and optionally having a carbonyl group, an ester bond, or an ether bond.

The resist composition containing such a polymer having the fluoroalcohol structure can improve coating uniformity of the resist film, and can promote the dissolution in the alkaline developer.

The inventive resist composition preferably further comprises an onium salt (E) represented by the following general formula (e-1), (e-1)

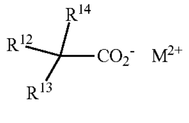

wherein $R^{12}$ and $R^{13}$ each independently represent a hydrogen atom, a fluorine atom, a hydrocarbon group having 1 to 10 carbon atoms and optionally having a fluorine atom, or a trifluoromethyl group;

$R^{14}$ represents a hydrogen atom, a hydroxy group, a substituted or unsubstituted linear alkyl group having 1 to 20 carbon atoms, a substituted or unsubstituted branched or cyclic alkyl group having 3 to 20 carbon atoms, the alkyl group optionally having an ether bond and an ester bond, or a substituted or unsubstituted aryl group having 6 to 30 carbon atoms; and $M^{2+}$ represents a counter cation having a substituent and being a sulfonium cation or an iodonium cation.

Adding such a low molecular-weight salt can inhibit the formation of the polymer composite formed by the ionic interaction between the polymers of the anion-introduced base polymer and the cation-introduced base polymer. Thus, the apparent molecular weight can be regulated.

The solvent (D) is preferably a mixed solvent of two or three solvents selected from propylene glycol monomethyl ether acetate, propylene glycol dimethyl ether, ethyl lactate, γ-butyrolactone, and 4-hydroxy-4-methyl-2-pentanone.

Using such a solvent can provide a resist composition having excellent coatability.

The present invention also provides a patterning process, comprising:

(i) a step of forming a resist film on a substrate by using the above resist composition;

(ii) a step of exposing the resist film to KrF excimer laser with a wavelength of 248 nm, ArF excimer laser with a wavelength of 193 nm, EUV lithography with a wavelength of 13.5 nm, or electron beam; and (iii) a step of developing the exposed resist film with an alkaline developer.

Such a patterning process forms the polymer composite, and can form a resist pattern having reduced edge roughness (LER and LWR) and size uniformity (CDU) of a hole pattern with high resolution, having good pattern shape after the exposure, and having excellent etching resistance.

Advantageous Effects of Invention

The inventive resist composition reduces the solubility in the alkaline developer and maintains the dissolution contrast even in a high exposure-dose region for pursuing resolution with considering the trade-off between sensitivity and resolution, and even using a base polymer having an introduced photoacid generator anion. Thus, the inventive resist composition exhibits high resolution, good pattern shape after the exposure, and good edge roughness. Therefore, the inventive resist composition can yield a resist composition, particularly a chemically amplified resist composition, suitable for a pattern forming material for particularly super LSI manufacturing or EUV exposure.

BRIEF DESCRIPTION OF EMBODIMENTS

As noted above, as a result of pursuing the high resolution, there has been demands for developments of a resist composition that can form a resist pattern having reduced edge roughness (LER and LWR) and size uniformity (CDU) of a hole pattern even with an increased exposure dose, having good pattern shape after the exposure, and having excellent etching resistance.

Earnest investigation has been made to achieve the above object, and consequently found are that a rigid film can be formed by forming a polymer composite having a large apparent molecular weight with an ionic interaction between the polymers of the anion-introduced base polymer and the cation-introduced base polymer, and that the resist composition can reduce solubility in an alkaline developer even in a high exposure-dose region and reduce edge roughness (LER and LWR) and size uniformity (CDU) of a hole pattern with high resolution to enable to fine processing with a good pattern shape. These findings has led to the completion of the present invention.

Specifically, the present invention is a resist composition, comprising:

a resin (A) having: a repeating unit represented by the following general formula (p-1); a repeating unit represented by the following general formula (a-1) and changing in its polarity by an action of an acid to be soluble in an alkaline aqueous solution; and a repeating unit represented by the following general formula (b-1);

a resin (B) having: a repeating unit represented by the following general formula (p-2); a repeating unit represented by the following general formula (a-1) and changing in its polarity by an action of an acid to be soluble in an alkaline aqueous solution; and a repeating unit represented by the following general formula (b-1); and a solvent (D), wherein a content of the resin (A) contained in the resist composition is smaller than a content of the resin (B), (p-1)

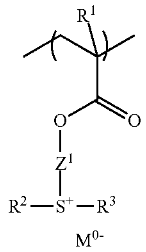

(p-2)

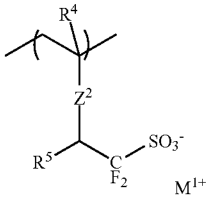

(a-1)

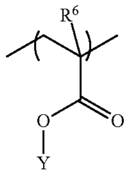

(b-1)

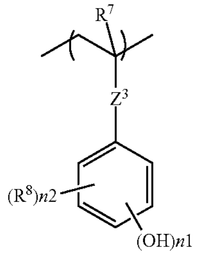

wherein in the general formula (p-1), $R^1$ represents a hydrogen atom or a methyl group;

$Z^1$ represents a single bond, a phenylene group, $—O—Z^{11}—$, $—C(=O)—O—Z^{11}—$, $—C(=O)—NH—Z^{11}—$, $—Z^{12}$-Ph-, $—Z^{12}—$O-Ph-, or $—Z^{12}—C(=O)—O$-Ph-; $Z^{11}$ represents an alkanediyl group having 1 to 6 carbon atoms, an alkenediyl group having 2 to 6 carbon atoms, or a phenylene group, $Z^{11}$ optionally having a carbonyl group, an ester bond, an ether bond, or a hydroxy group; $Z^{12}$ represents a hydrocarbon group having 1 to 15 carbon atoms; Ph represents a phenylene group;

$R^2$ and $R^3$ each independently represents a monovalent hydrocarbon group having 1 to 20 carbon atoms and optionally having a heteroatom, or a phenyl group;

$M^{0-}$ represents a non-nucleophilic counterion;

in the general formula (p-2), $R^4$ represents a hydrogen atom or a methyl group;

$Z^2$ represents a single bond, a phenylene group, $—O—Z^{21}—$, $—C(=O)—O—Z^{21}—$, $—Z^{21}—C(=O)—O—$, or $—C(=O)—NH—Z^{21}—$; $Z^{21}$ represents a single bond, an alkanediyl group having 1 to 20 carbon atoms, an alkenediyl group having 2 to 20 carbon atoms, or a phenylene group, $Z^{21}$ optionally having a carbonyl group, an ester bond, an ether bond, or a hydroxy group;

$M^{1+}$ represents a counter cation having a substituent and being a sulfonium cation, an iodonium cation, or an ammonium cation;

$R^5$ represents a hydrogen atom or a trifluoromethyl group;

in the general formula (a-1), $R^6$ represents a hydrogen atom or a methyl group;

Y represents a group having a structure changing in its polarity by an action of an acid to be soluble in an alkaline aqueous solution;

in the general formula (b-1), $R^7$ represents a hydrogen atom or a methyl group;

$Z^3$ represents a single bond, a methylene group, an ethylene group, a phenylene group, a fluorinated phenylene group, an ester bond, an amide bond, $—O—Z^{31}—$, $—C(=O)—O—Z^{31}—$, or $—C(=O)—NH—Z^{31}—$; $Z^{31}$ represents an alkanediyl group having 1 to 12 carbon atoms and optionally having a carbonyl group, an ester bond, or an ether bond;

"n1" represents an integer of 1 to 3; "n2" represents an integer of 0 to 3; a total of "n1" and "n2" is 5 or less; and $R^8$ represents a halogen atom, a linear hydrocarbon group having 1 to 10 carbon atoms, or a branched or cyclic hydrocarbon group having 3 to 10 carbon atoms, and $—CH_2—$ constituting these groups are optionally substituted with $—O—$, $—C(=O)—O—$, or $—C(=O)—$, or optionally substituted with a hydrogen atom, a halogen atom, or a heteroatom.

Hereinafter, the present invention will be described in detail, but the present invention is not limited thereto.

Resist Composition

The inventive resist composition provides a resist composition comprising:

a resin (A) having: a repeating unit represented by the following general formula (p-1); a repeating unit represented by the following general formula (a-1) and changing in its polarity by an action of an acid to be soluble in an alkaline aqueous solution; and a repeating unit represented by the following general formula (b-1);

a resin (B) having: a repeating unit represented by the following general formula (p-2); a repeating unit represented by the following general formula (a-1) and changing in its polarity by an action of an acid to be soluble in an alkaline aqueous solution; and a repeating unit represented by the following general formula (b-1); and a solvent (D), wherein a content of the resin (A) contained is smaller than a content of the resin (B);

(p-1)

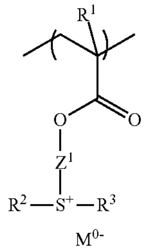

(p-2)

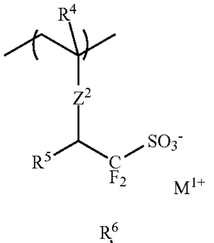

(a-1)

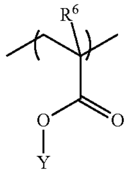

(b-1)

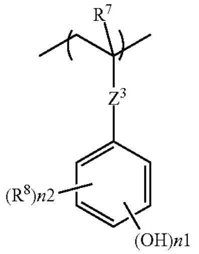

wherein in the general formula (p-1), $R^1$ represents a hydrogen atom or a methyl group;

$Z^1$ represents a single bond, a phenylene group, —O—$Z^{11}$—, —C(═O)—O—$Z^{11}$—, —C(═O)—NH—$Z^{11}$—, —$Z^{12}$-Ph-, —$Z^{12}$—O-Ph-, or —$Z^{12}$—C(═O)—O-Ph-; $Z^{11}$ represents an alkanediyl group having 1 to 6 carbon atoms, an alkenediyl group having 2 to 6 carbon atoms, or a phenylene group, $Z^{11}$ optionally having a carbonyl group, an ester bond, an ether bond, or a hydroxy group; $Z^{12}$ represents a hydrocarbon group having 1 to 15 carbon atoms; Ph represents a phenylene group;

$R^2$ and $R^3$ each independently represents a monovalent hydrocarbon group having 1 to 20 carbon atoms and optionally having a heteroatom, or a phenyl group;

$M^{0-}$ represents a non-nucleophilic counterion;

in the general formula (p-2), $R^4$ represents a hydrogen atom or a methyl group;

$Z^2$ represents a single bond, a phenylene group, —O—$Z^{21}$—, —C(═O)—O—$Z^{21}$—, —$Z^{21}$—C(═O)—O—, or —C(═O)—NH—$Z^{21}$—; $Z^{21}$ represents a single bond, an alkanediyl group having 1 to 20 carbon atoms, an alkenediyl group having 2 to 20 carbon atoms, or a phenylene group, $Z^{21}$ optionally having a carbonyl group, an ester bond, an ether bond, or a hydroxy group;

$M^{1+}$ represents a counter cation having a substituent and being a sulfonium cation, an iodonium cation, or an ammonium cation;

$R^5$ represents a hydrogen atom or a trifluoromethyl group;

in the general formula (a-1), $R^6$ represents a hydrogen atom or a methyl group;

Y represents a group having a structure changing in its polarity by an action of an acid to be soluble in an alkaline aqueous solution;

in the general formula (b-1), $R^7$ represents a hydrogen atom or a methyl group;

$Z^3$ represents a single bond, a methylene group, an ethylene group, a phenylene group, a fluorinated phenylene group, an ester bond, an amide bond, —O—$Z^{31}$—, —C(═O)—O—$Z^{31}$—, or —C(═O)—NH—$Z^{31}$—; $Z^{31}$ represents an alkanediyl group having 1 to 12 carbon atoms and optionally having a carbonyl group, an ester bond, or an ether bond;

"n1" represents an integer of 1 to 3; "n2" represents an integer of 0 to 3; a total of "n1" and "n2" is 5 or less; and $R^8$ represents a halogen atom, a linear hydrocarbon group having 1 to 10 carbon atoms, or a branched or cyclic hydrocarbon group having 3 to 10 carbon atoms, and —$CH_2$— constituting these groups are optionally substituted with —O—, —C(═O)—O—, or —C(═O)—, or optionally substituted with a hydrogen atom, a halogen atom, or a heteroatom.

The above polymer compound generates an acid by sensitization to high-energy ray or heat.

Examples of the high-energy ray in the present invention include ultraviolet ray, far ultraviolet ray, electron beam, EUV (extreme ultraviolet ray), X-ray, excimer laser, γ-ray, and synchrotron radiation.

As described below, characteristics corresponding to each of the above repeating units are imparted to the resist film obtained from this composition.

When the (meth)acrylate ester having the acid-labile group of the repeating unit (a-1) has a rather compact acid-labile group, a swelling amount due to the alkaline developer is smaller after eliminating the acid-labile group by the generated acid, resulting in reduced pattern collapse.

With the inventive resist composition in which the polymer compound has the anion portion of the photoacid generator, the repeating unit (p-2) has higher effect of inhibiting the acid diffusion than a conventional additive-type photoacid generator. Thus, a resist composition having high resolution, exposure latitude, excellent process applicability, and good pattern shape after the exposure can be obtained. The acid has acidity that can eliminate the acid-labile group by baking the (meth)acrylate ester having the acid-labile group at a temperature of 150° C. or lower.

A conventional polymer compound, which has an anion portion of a weak acid group, has considerably poor solubility in a resist solvent and aggregates during the polymer synthesis, and it is difficult to introduce a repeating unit having the anion portion of the weak acid group at a high proportion. Accordingly, in the present invention, the polymer compound has the cation portion to have excellent solvent solubility and to enable to form a salt with the weak acid. The distribution in the film and process applicability are excellent, and the pattern shape after the exposure is good.

The inventive resist composition, which mixes the base polymer having the introduced anion of the repeating unit (p-2) and the base polymer having the introduced cation of the repeating unit (p-1), can form a rigid film with the ionic interaction between the polymers. The solubility in the alkaline developer is reduced even in the high exposure-dose region, edge roughness (LER and LWR) and size uniformity (CDU) of a hole pattern is reduced with high resolution, and the pattern shape is good.

As a quencher component of the repeating unit (p-1) that can be contained in the inventive resist composition, combination with a weak acid onium salt (e-0) compared with an α-fluoroalkanesulfonic acid can prevent change in a concentration in a surface layer of a resist film during a baking process in the resist film formation or the patterning, and can improve rectangular formability. This is because the weak acid onium salt is typically nonvolatile compared with nitrogen-containing compounds such as amines. In addition, as the weak acid onium salt, using a carboxylate onium salt (e-1) having lower acidity and higher quencher ability than an alkanesulfonic acid having no fluorine atom at the α-position yields high effect of inhibiting the acid diffusion, high resolution, exposure latitude, and excellent process applicability. Adding the weak acid onium salt inhibits the ionic interaction between the polymers of the anion-introduced base polymer and the cation-introduced base polymer, and the composite having appropriate resist performance can be regulated.

From the viewpoint of the dissolution contrast with the alkaline developer, the inventive resist composition allows the polymer to generate the anion portion to increase the solubility in the alkaline developer. The anion portion is generated by decomposing the (meth)acrylate which is to generate a carboxylic acid and protected with the acid-labile group, or by decomposing the cation by exposure. When the acid-labile group in the polymer is eliminated at a low exposure dose, the cation is decomposed by the exposure to generate the anion portion, and the contribution to the solubility is negligible. However, when the cation is decomposed with a larger exposure dose to generate the anion portion, the contribution to the solubility may be not negligible.

The phenol group of the repeating unit (b-1) has sensitizing effect to EB and EUV, and has a swelling inhibition effect in the alkaline developer. The polymer compound having the phenol group improves generation efficiency of secondary electrons and the sensitizing effect during the exposure of the resist composition, and the decomposition efficiency of the acid generator is increased to improve sensitivity.

In the solvent contained in the inventive resist composition, increasing a proportion of a polar solvent can inhibit decrease in the solubility of the mixture of the anion-introduced base polymer and the cation-introduced base polymer in a conventional resist solvent, resulting in improvement of the solubility.

The inventive resist composition has the above configuration to be a resist composition that can form a pattern having reduced solubility in the alkaline developer even in a high exposure-dose region, having reduced edge roughness (LER and LWR) and size uniformity (CDU) of a hole pattern with high resolution, and having good pattern shape.

Hereinafter, each constituent in the inventive resist composition will be described.

<Resin (A)>

Repeating Unit (p-1)

The resin (A) constituting the inventive resist composition has the following general formula (p-1) as a repeating unit.

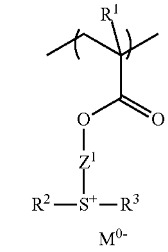

(p-1)

In the general formula (p-1), $R^1$ represents a hydrogen atom or a methyl group;

$Z^1$ represents a single bond, a phenylene group, —O—$Z^{11}$—, —C(═O)—O—$Z^{11}$—, —C(═O)—NH—$Z^{11}$—, —$Z^{12}$-Ph-, —$Z^{12}$—O-Ph-, or —$Z^{12}$—C(═O)—O-Ph-; $Z^{11}$ represents an alkanediyl group having 1 to 6 carbon atoms, an alkenediyl group having 2 to 6 carbon atoms, or a phenylene group, $Z^{11}$ optionally having a carbonyl group, an ester bond, an ether bond, or a hydroxy group; $Z^{12}$ represents a hydrocarbon group having 1 to 15 carbon atoms; Ph represents a phenylene group;

$R^2$ and $R^3$ each independently represents a monovalent hydrocarbon group having 1 to 20 carbon atoms and optionally having a heteroatom, or a phenyl group; and $M^{0-}$ represents a non-nucleophilic counterion.

Examples of a monomer to yield the repeating unit (p-1) include the following monomers, but the monomer is not limited thereto.

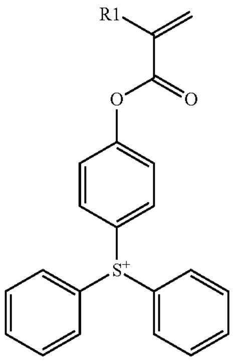

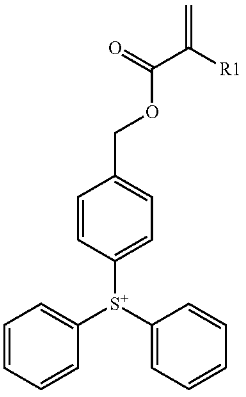

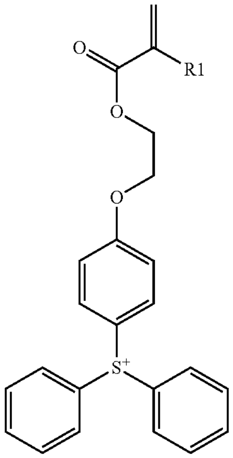

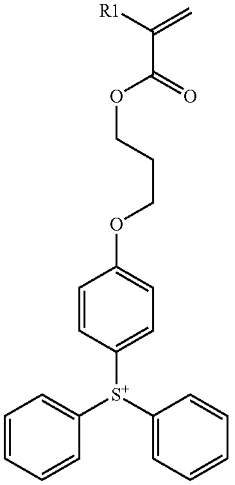

-continued
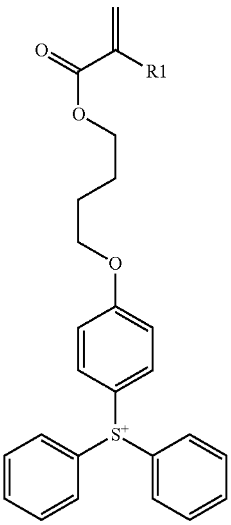
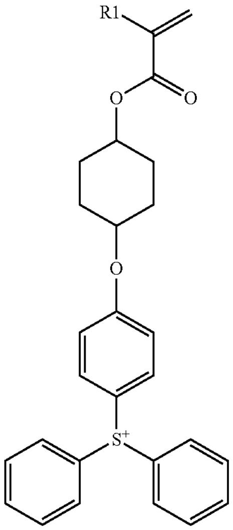
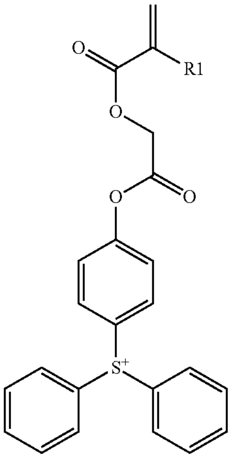
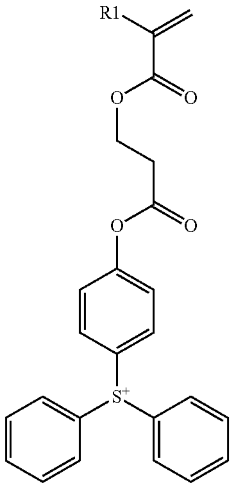
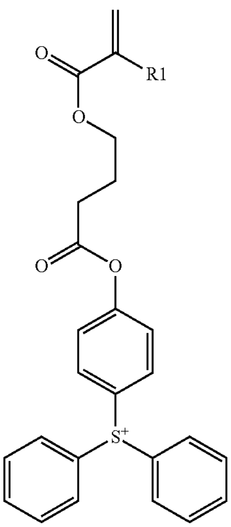
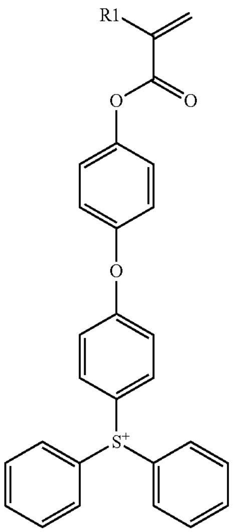
-continued
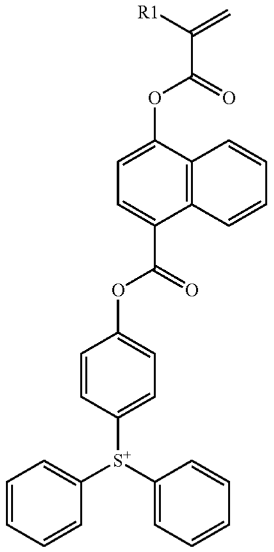
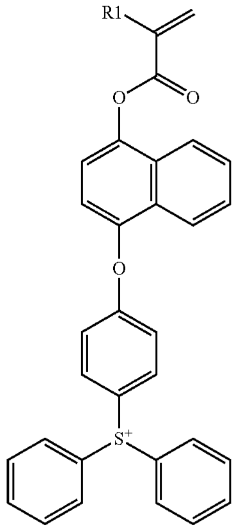
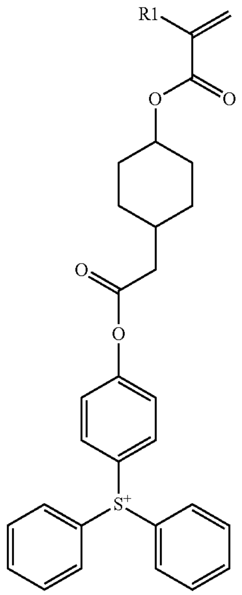
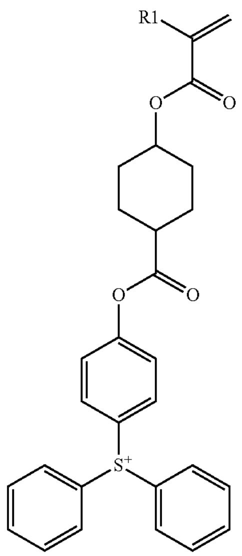
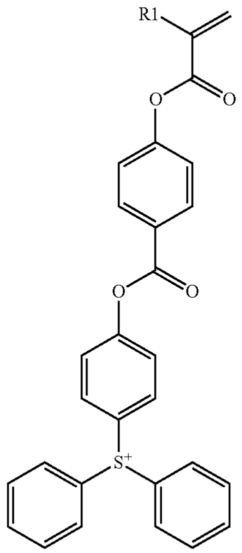
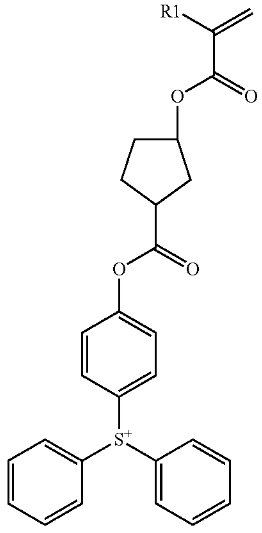

-continued

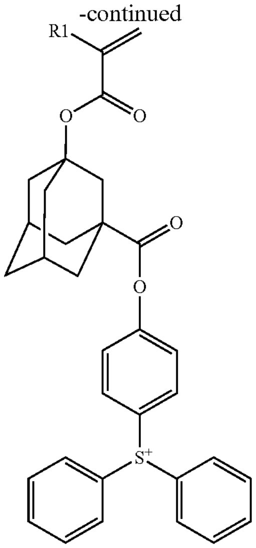

Examples of the non-nucleophilic counterion $M^{0-}$ include: halide ions, such as a chloride ion and a bromide ion; fluoroalkylsulfonates, such as triflate, 1,1,1-trifluoroethanesulfonate, and nonafluorobutanesulfonate; arylsulfonates, such as tosylate, benzenesulfonate, 4-fluorobenzenesulfonate, and 1,2,3,4,5-pentafluorobenzenesulfonate; alkylsulfonates, such as mesylate and butanesulfonate; ions of sulfonimides, such as bis(trifluoromethylsulfonyl)imide, bis(perfluoroethylsulfonyl)imide, and bis(perfluorobutylsulfonyl)imide; sulfonmethides, such as tris(tifluoromethylsulfonyl)methide and tris(perfluoroethylsulfonyl)methide; fluoroalkylcarboxylates, such as trifluoromethylcarboxylate and nonfluorobutanecarboxylate; and alkylcarboxylates, such as methylcarboxylate and benzenecarboxylate.

Examples of the non-nucleophilic counterion $M^{0-}$ include the following structures, but the non-nucleophilic counterion $M^{0-}$ is not limited thereto.

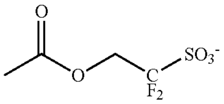
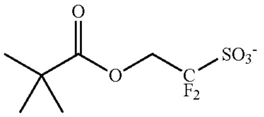
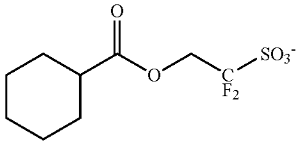
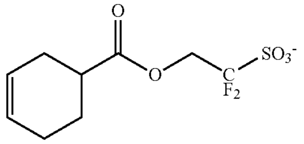
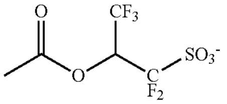
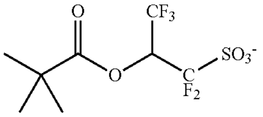
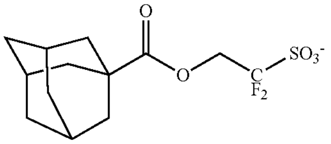

-continued

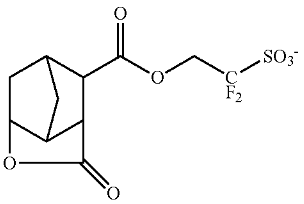
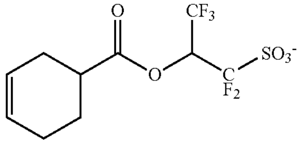
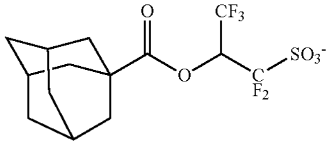
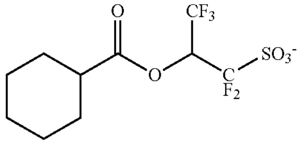
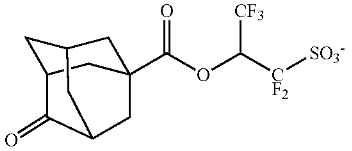
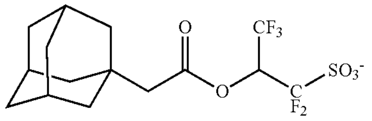
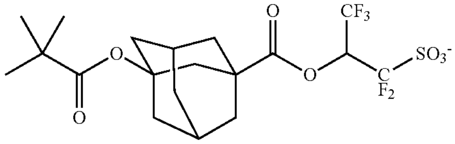
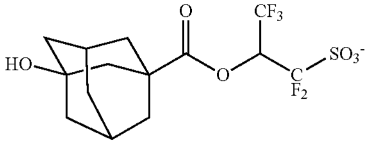
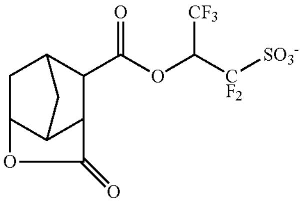
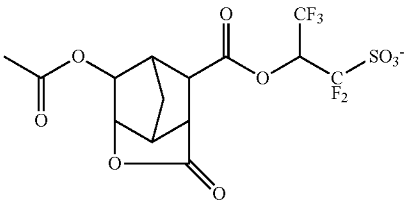

-continued

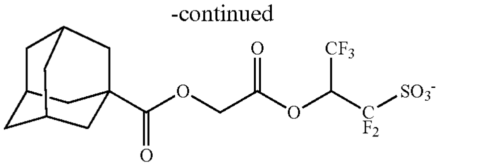

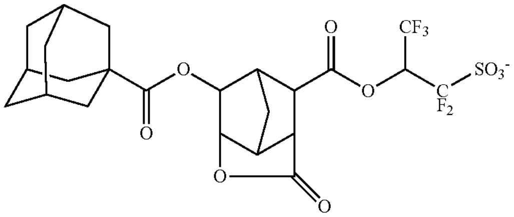

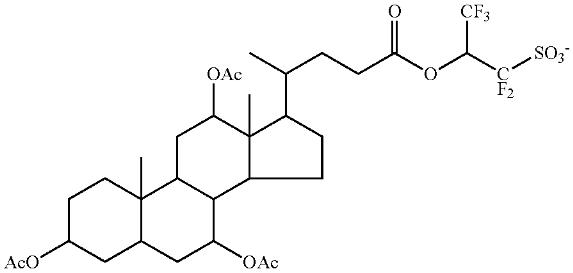

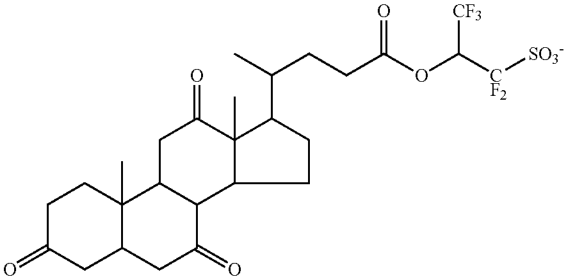

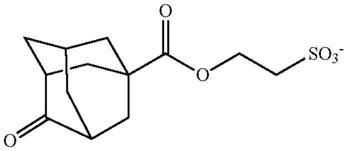

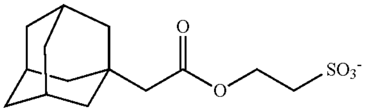

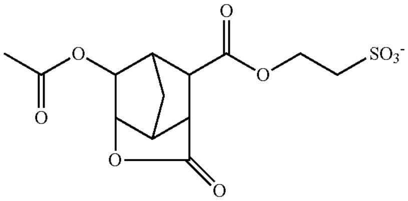

The ion $M^{0-}$ preferably represents a structure represented by the following general formula (e-0).

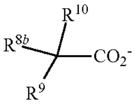

(e-0)

In the formula (e-o), $R^{8b}$ and $R^9$ each independently represent a hydrogen atom, a fluorine atom, or a trifluoromethyl group.

$R^{10}$ represents a hydrogen atom, a hydroxy group, a substituted or unsubstituted linear alkyl group having 1 to 20 carbon atoms, a substituted or unsubstituted branched or cyclic alkyl group having 3 to 20 carbon atoms, or a substituted or unsubstituted aryl group having 6 to 30 carbon atoms.

Specific examples of the structures represented by (e-0) include the following structures, but the structure is not limited thereto.

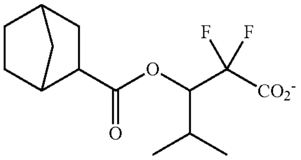

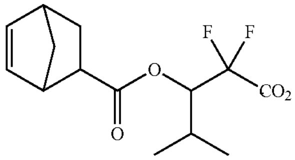

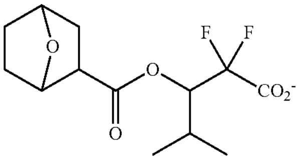

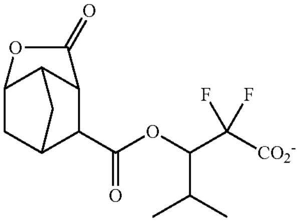

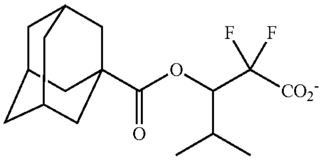

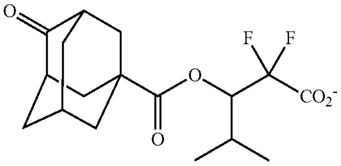

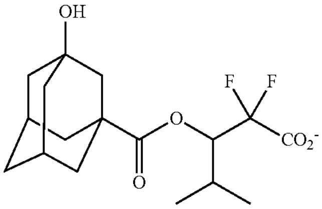

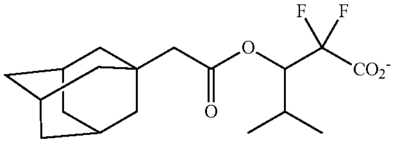

-continued
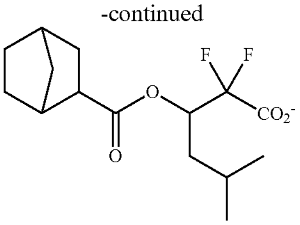
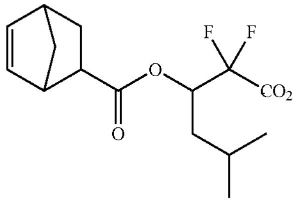
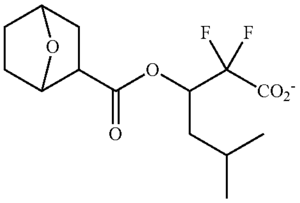
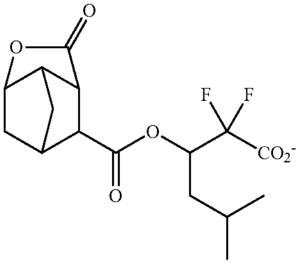
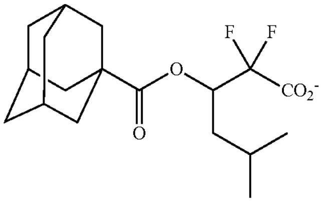
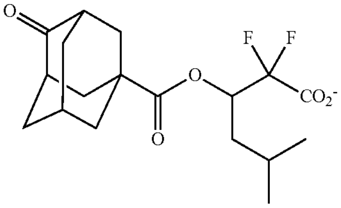
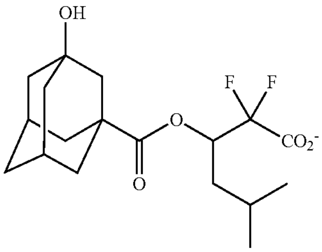
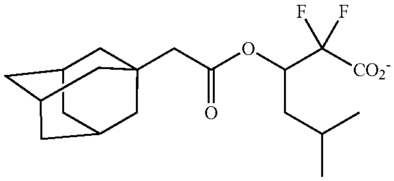
-continued
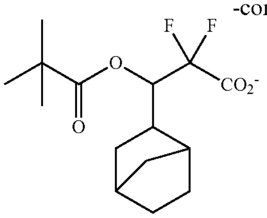
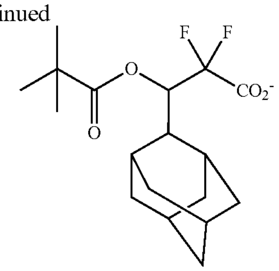
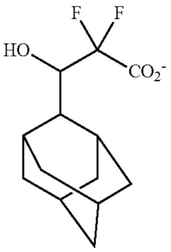
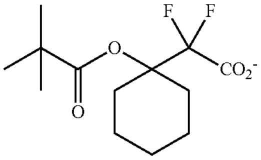
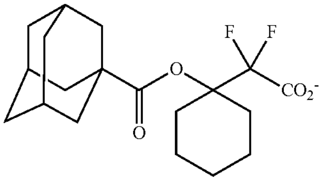
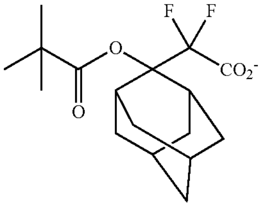
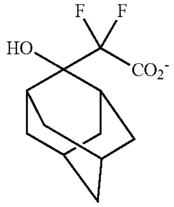
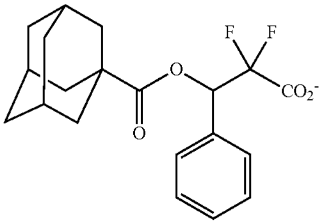
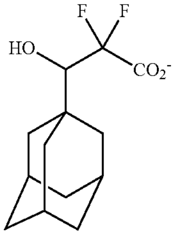
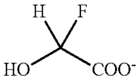
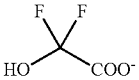
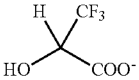
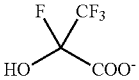
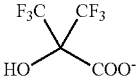
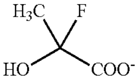
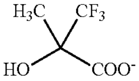
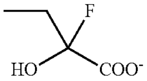
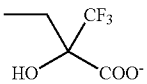
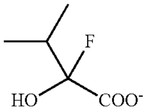
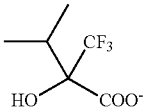
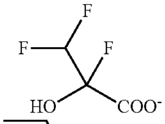
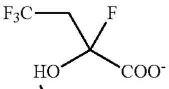
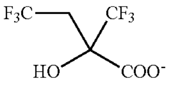
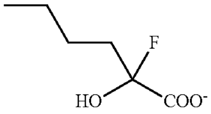
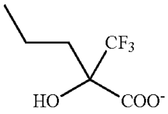
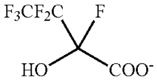
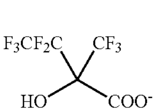
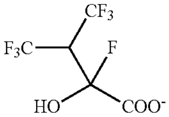
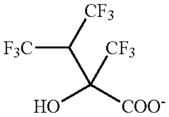

-continued

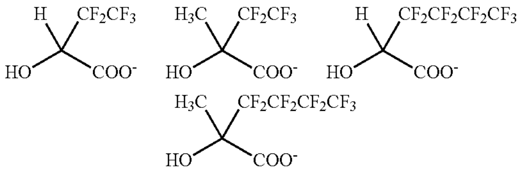

A carboxylic acid has lower acid strength than a sulfonium salt to generate an alkanesulfonic acid in which the α-position of the sulfonic acid is substituted with a fluorine atom, and than an alkanesulfonic acid in which the α-position of the sulfonic acid is not substituted with a fluorine atom. Thus, a cation of the carboxylic acid causes salt-exchange with the alkanesulfonic acid in which the α-position of the sulfonic acid is substituted with a fluorine atom contained in a polymer compound such as the polymer compound having the repeating unit (p-2), for example, and the carboxylic acid serves like a quencher. A carboxylic acid having lower acid strength has larger quenching ability and increases the contrast, resulting in excellent rectangular formability and edge roughness of the pattern after the development.

A composition rate of the repeating unit (p-1), which is a repeating unit ratio (p-1), relative to the total of all the repeating units of the polymer compound constituting the inventive resist composition in which the total is 1 satisfies $0<(p\text{-}1)\leq 0.5$.

Repeating Unit (a-1)

The polymer compound constituting the inventive resist composition has a repeating unit changing in its polarity by an action of an acid and represented by the following general formula (a-1),

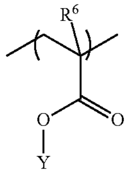

(a-1)

wherein $R^6$ represents a hydrogen atom or a methyl group; and

Y represents a group having a structure changing in its polarity by an action of an acid to be soluble in an alkaline aqueous solution.

Specific examples of a monomer to yield the repeating unit (a-1) include the following monomers, but the monomer is not limited thereto.

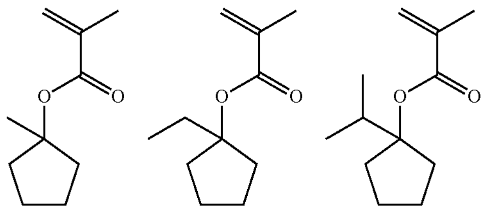

-continued

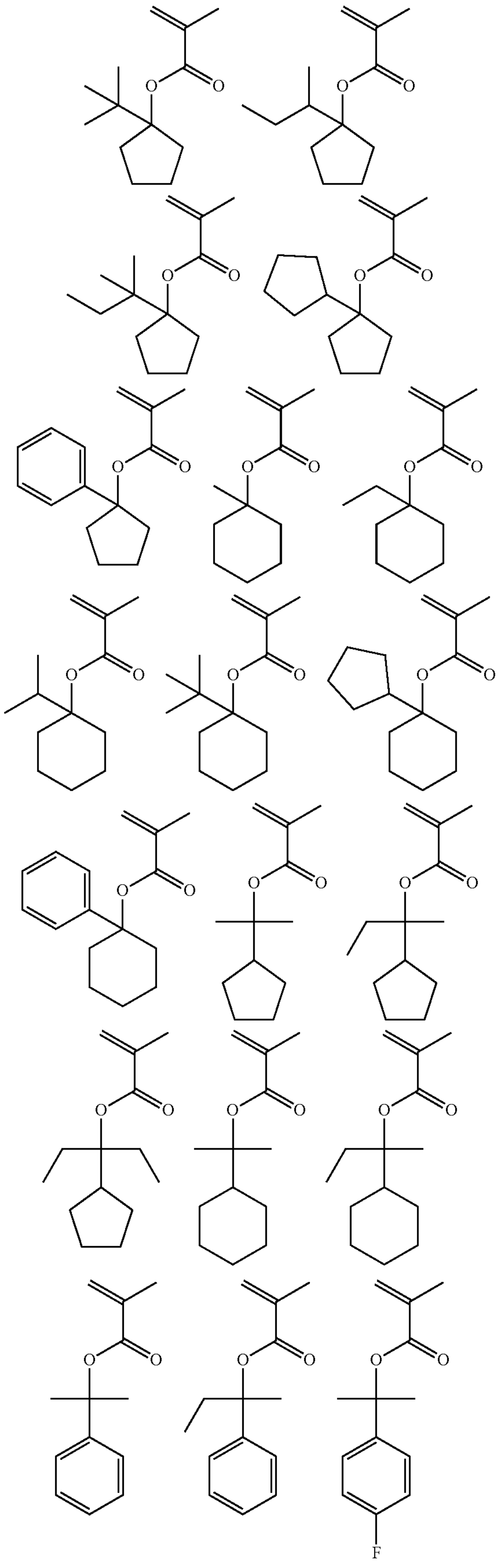

-continued

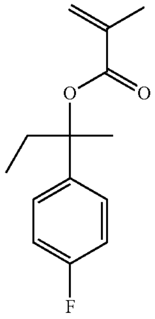
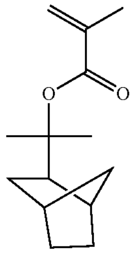
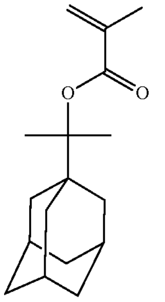
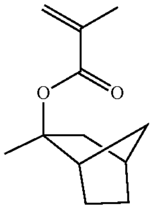
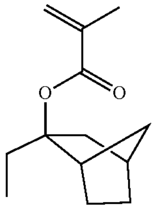
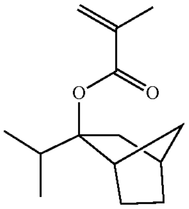
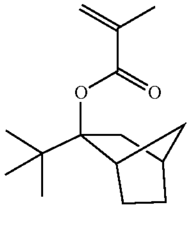
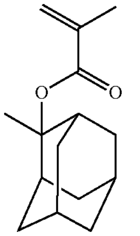
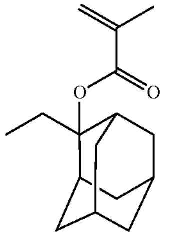
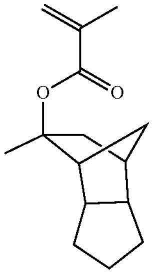
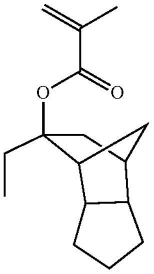
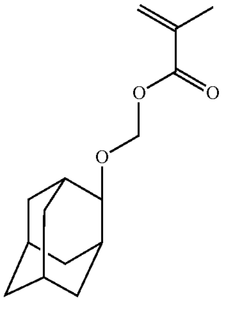
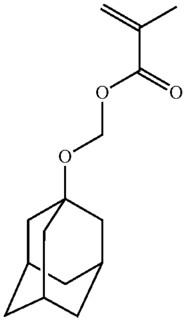
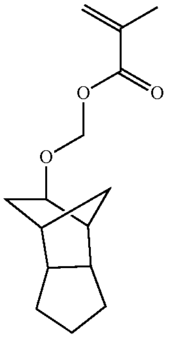
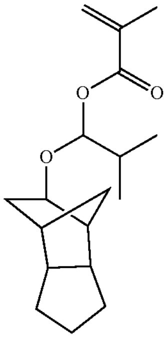

-continued

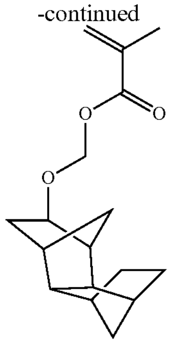

Repeating Unit (b-1)

The polymer compound constituting the inventive resist composition has a repeating unit represented by the following general formula (b-1), (b-1)

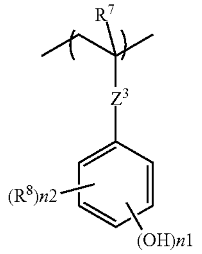

wherein $R^7$ represents a hydrogen atom or a methyl group;

$Z^3$ represents a single bond, a methylene group, an ethylene group, a phenylene group, a fluorinated phenylene group, an ester bond, an amide bond, $-O-Z^{31}-$, $-C(=O)-O-Z^{31}-$, or $-C(=O)-NH-Z^{31}-$; $Z^{31}$ represents an alkanediyl group having 1 to 12 carbon atoms and optionally having a carbonyl group, an ester bond, or an ether bond;

"n1" represents an integer of 1 to 3; "n2" represents an integer of 0 to 3; a total of "n1" and "n2" is 5 or less; and $R^8$ represents a halogen atom, a linear hydrocarbon group having 1 to 10 carbon atoms, or a branched or cyclic hydrocarbon group having 3 to 10 carbon atoms, and $-CH_2-$ constituting these groups are optionally substituted with $-O-$, $-C(=O)-O-$, or $-C(=O)-$, or optionally substituted with a hydrogen atom, a halogen atom, or a heteroatom.

Specific examples of the general formula (b-1) include the following repeating units, but the repeating unit is not limited thereto.

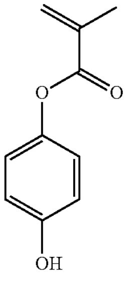
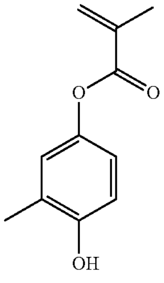
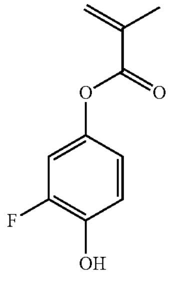

-continued
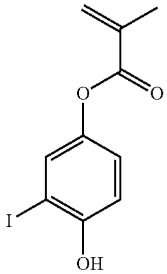 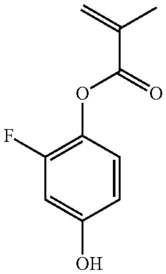 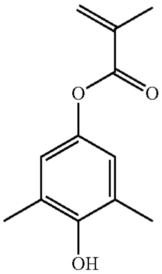
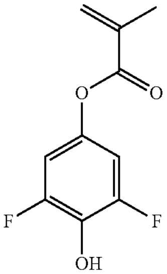 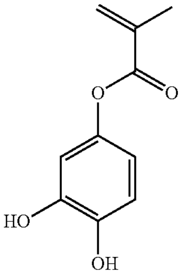 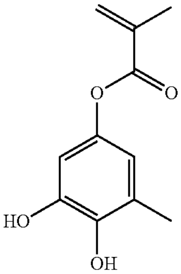
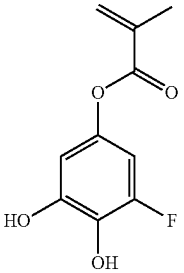 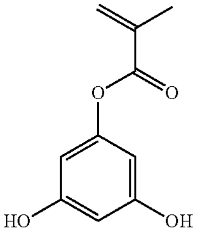
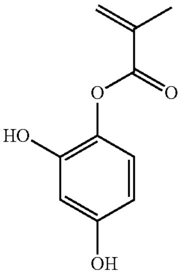 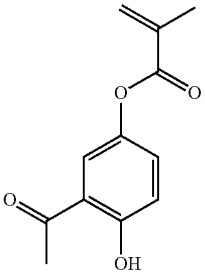
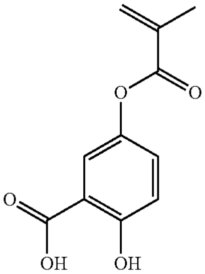 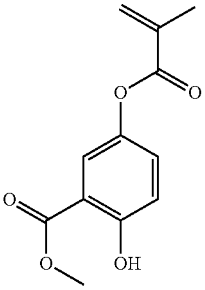
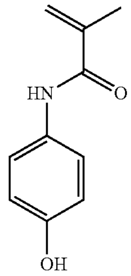 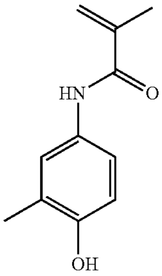 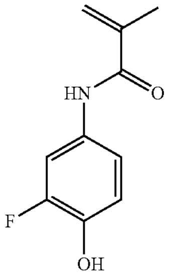
-continued
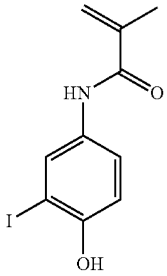 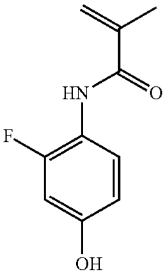 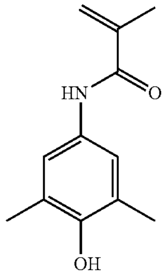
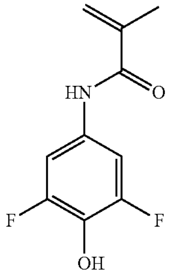 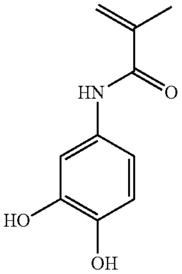 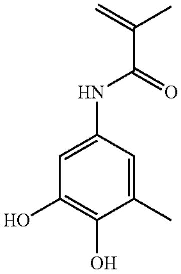
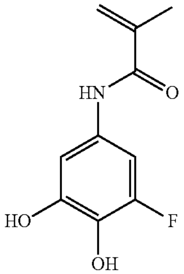 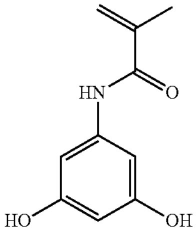
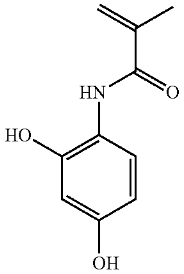 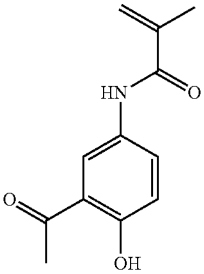
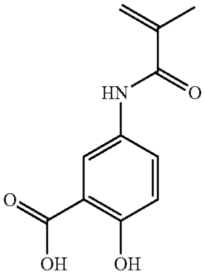 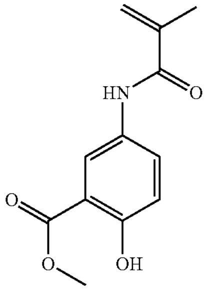
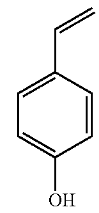 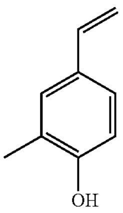

-continued

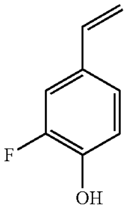 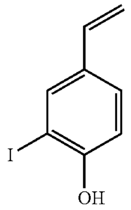 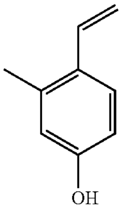 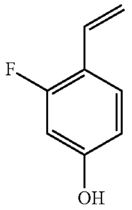

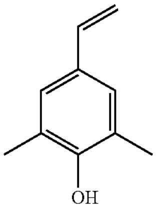 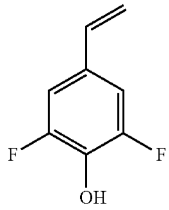 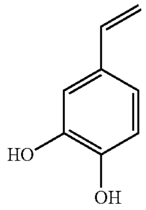

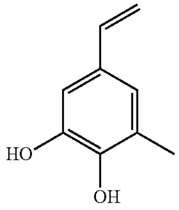 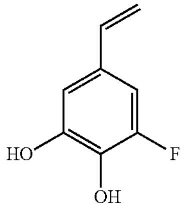

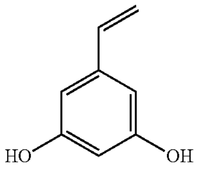 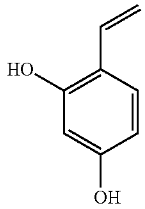

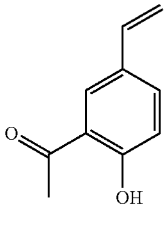 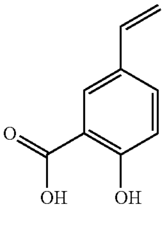 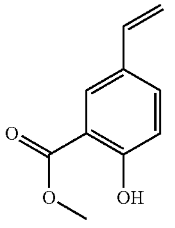

Since a compound having a phenolic hydroxy group has the sensitizing effect, the inventive resist composition has excellent sensitivity and CDU.

Lactone Structure

The resin (A) may have a repeating unit having a lactone structure.

The resin (A), however, may not have a repeating unit having a lactone structure.

The resist composition containing the resin (A) having no lactone structure can inhibit permeating the alkali developer into the pattern to inhibit swelling, and provide a resist pattern having further preferable shape.

<Resin (B)>

Repeating Unit (p-2)

The resin (B) constituting the inventive resist composition has a repeating unit represented by the following general formula (p-2).

(p-2)

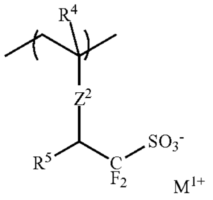

In the general formula, $R^4$ represents a hydrogen atom or a methyl group;

$Z^2$ represents a single bond, a phenylene group, —O—$Z^{21}$—, —C(═O)—O—$Z^{21}$—, —$Z^{21}$—C(═O)—O—, or —C(═O)—NH—$Z^{21}$—; $Z^{21}$ represents a single bond, an alkanediyl group having 1 to 20 carbon atoms, an alkenediyl group having 2 to 20 carbon atoms, or a phenylene group, $Z^{21}$ optionally having a carbonyl group, an ester bond, an ether bond, or a hydroxy group;

$M^{1+}$ represents a counter cation having a substituent and being a sulfonium cation, an iodonium cation, or an ammonium cation; and $R^5$ represents a hydrogen atom or a trifluoromethyl group.

Examples of the structure of the anion-introduced repeating unit monomer excluding $M^{1+}$ of (p-2) include the following structures, but the structure is not limited thereto.

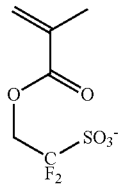 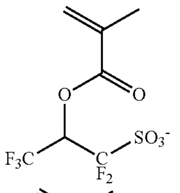

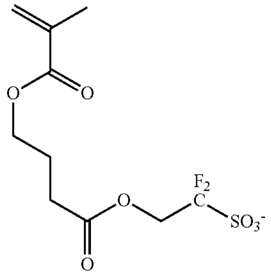 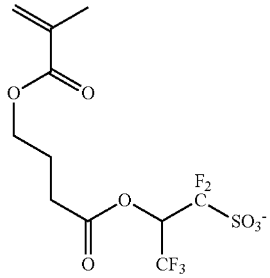

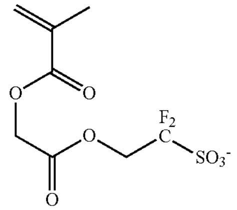 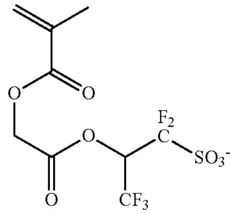

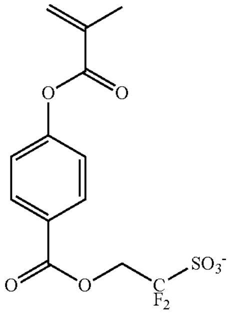 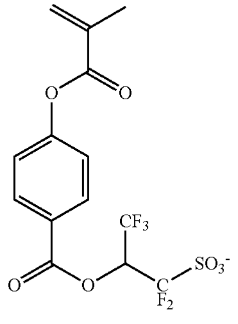

-continued

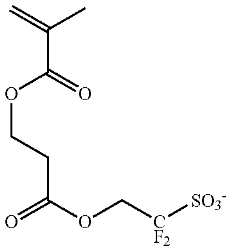

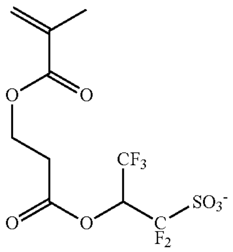

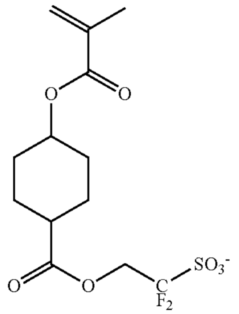

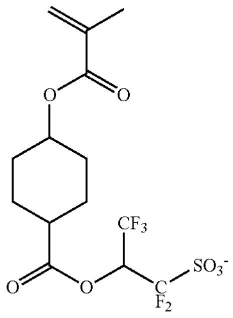

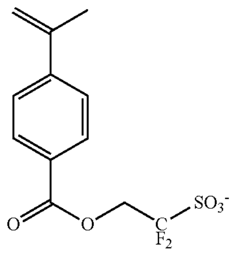

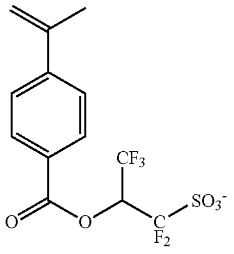

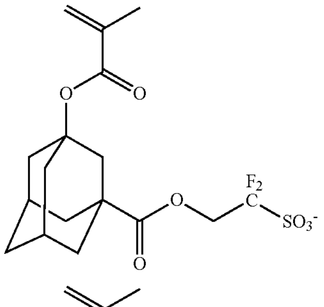

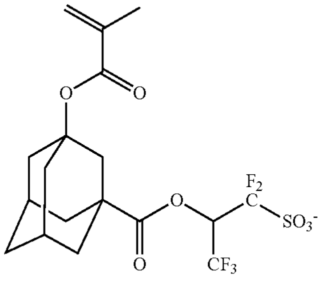

-continued

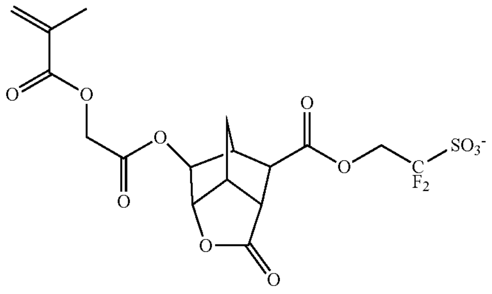

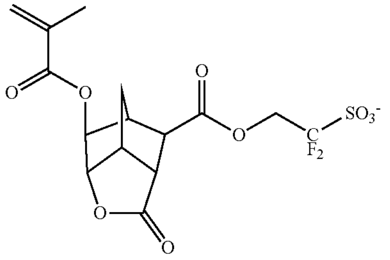

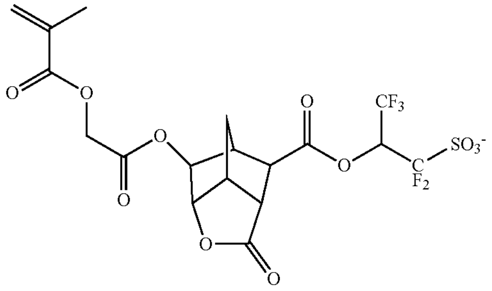

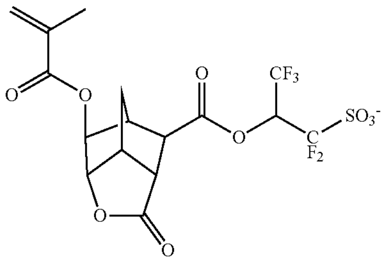

Examples of the sulfonium cation of $M^{1+}$ include the following cations, but the sulfonium cation is not limited thereto. In the following formulae, Me represents a methyl group, nBu represents an n-butyl group, and tBu represents a tert-butyl group.

Examples of the iodonium cation of $M^{1+}$ include the following cations, but the iodonium cation is not limited thereto. In the following formulae, tBu represents a tert-butyl group, and Ph represents a phenyl group.

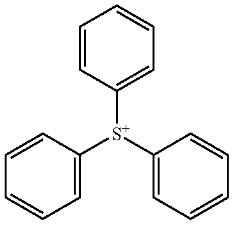

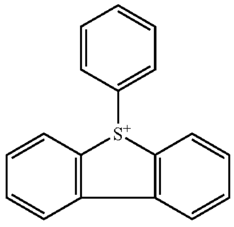

-continued
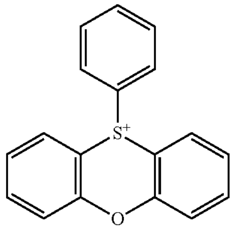
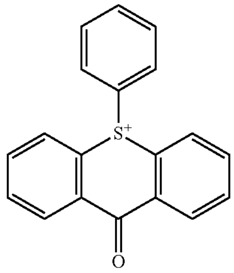
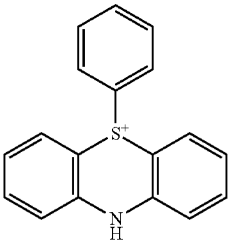
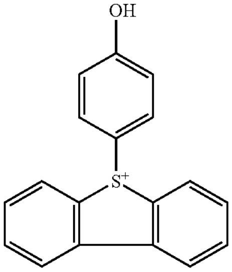
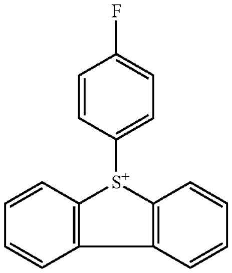
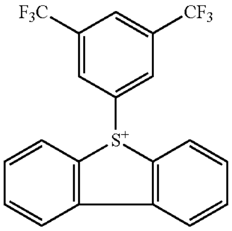
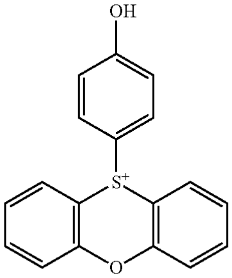
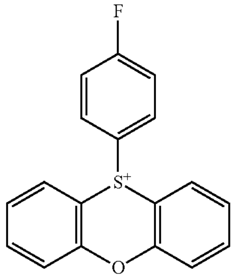
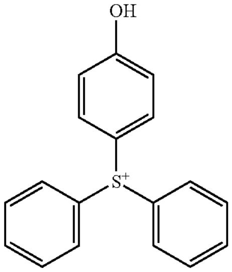
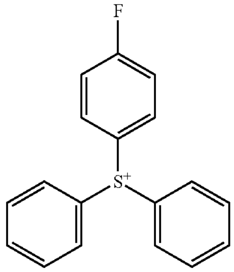
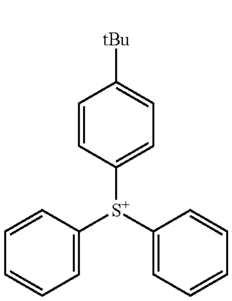
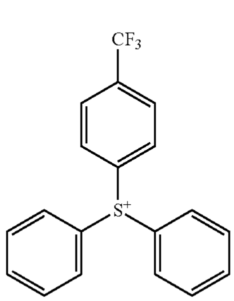
-continued
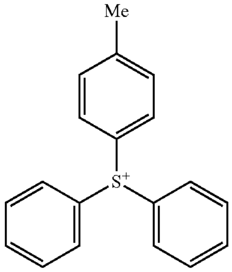
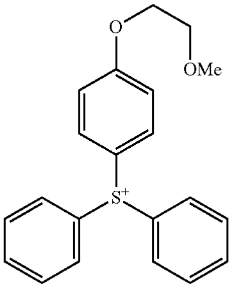
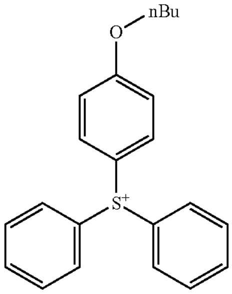
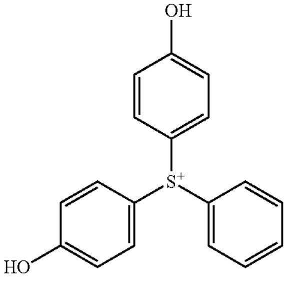
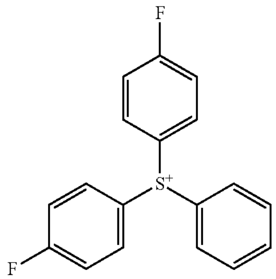
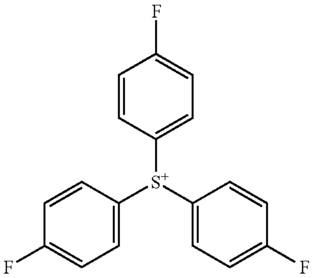
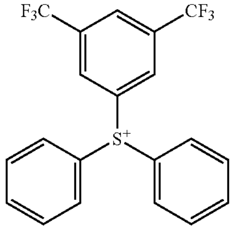
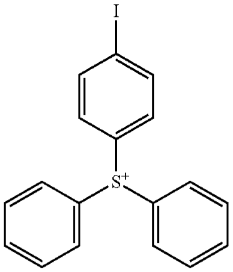
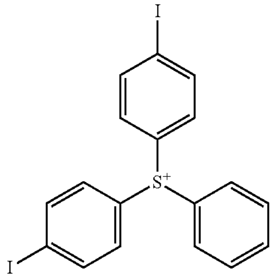
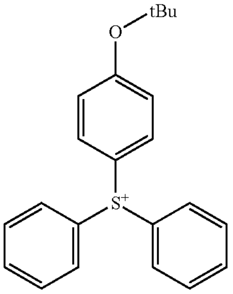
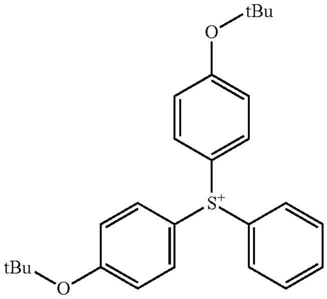

-continued
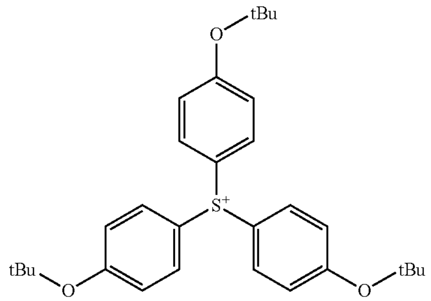
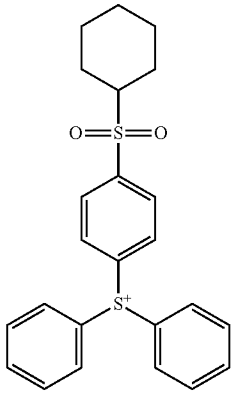
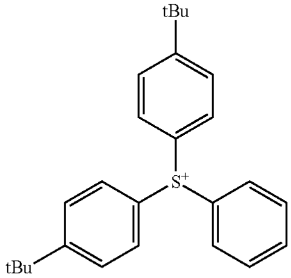
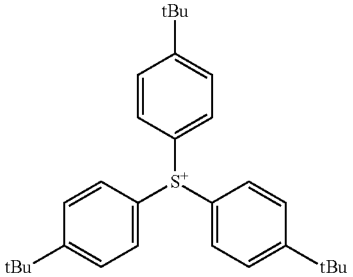
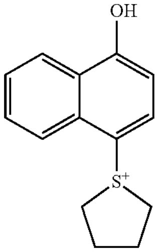
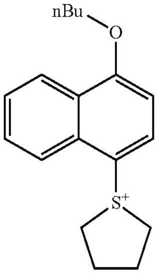
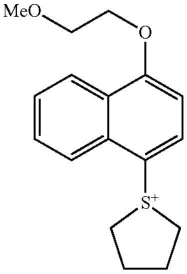
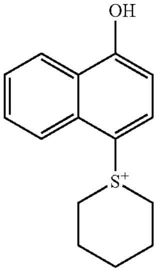
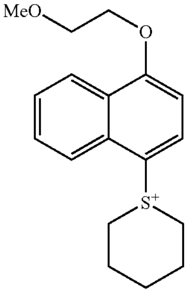
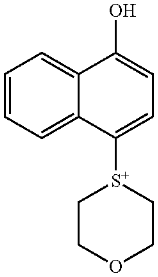
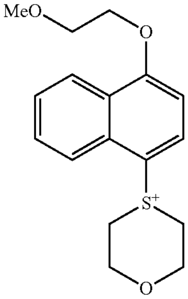
-continued
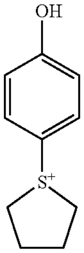
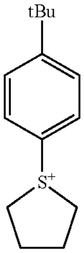
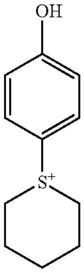
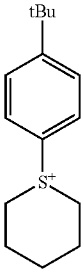
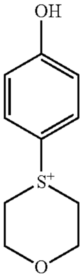
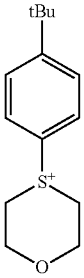
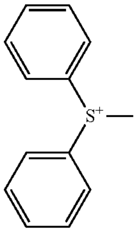
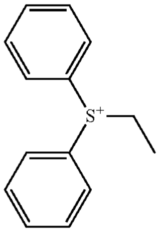
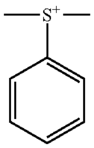
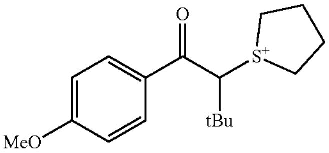
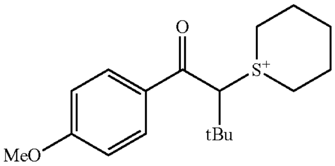
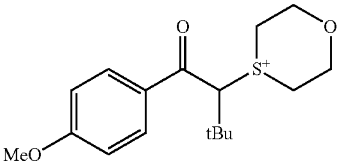
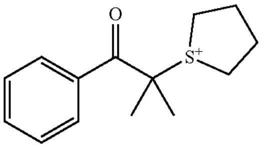
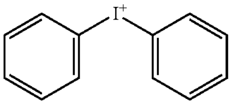
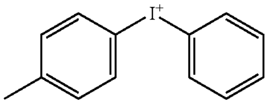
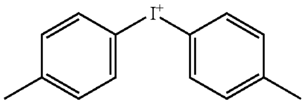
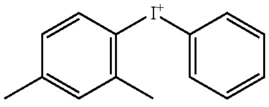
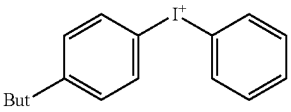
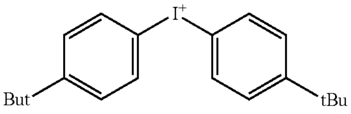
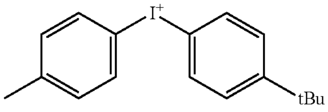

-continued
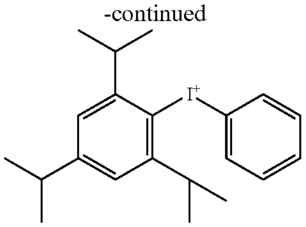
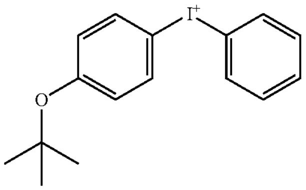
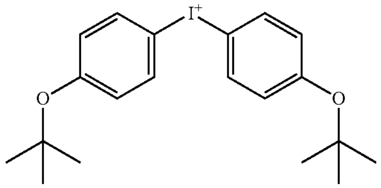
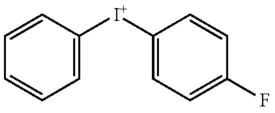
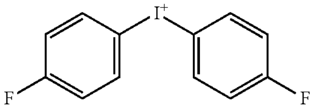
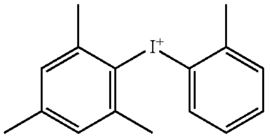
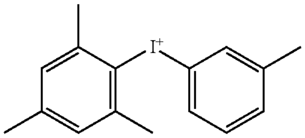
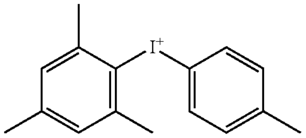
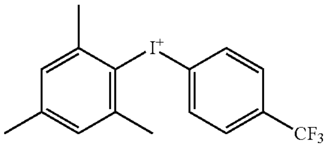
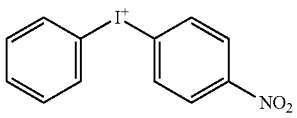
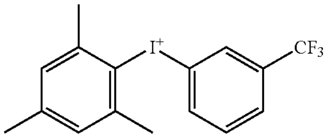
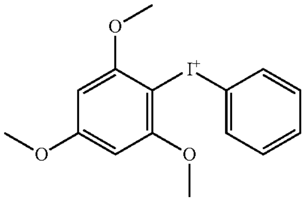
-continued
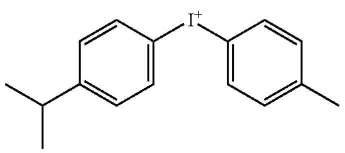
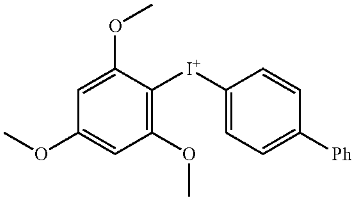
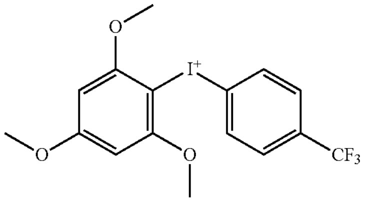
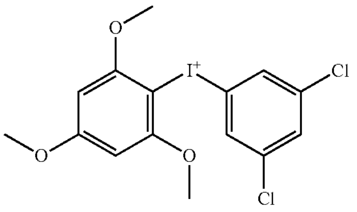
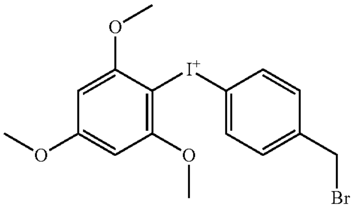
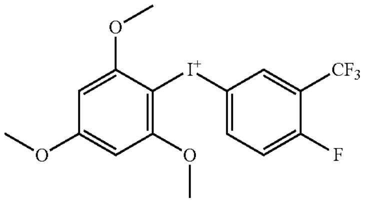
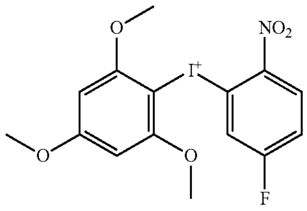
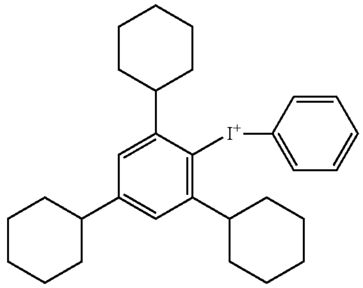

-continued

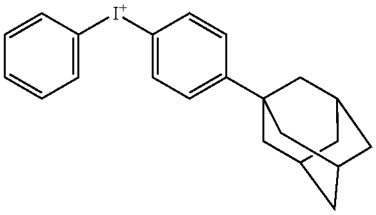

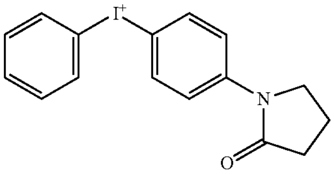

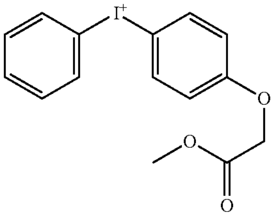

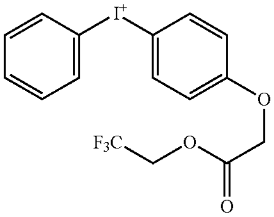

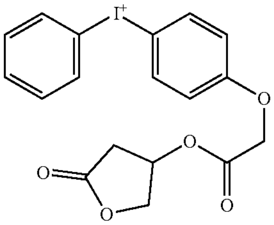

Specific examples of the ammonium cation of $M^{1+}$ include the following cations, but the ammonium cation is not limited thereto.

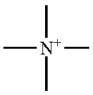

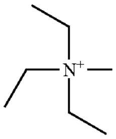

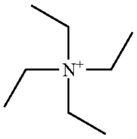

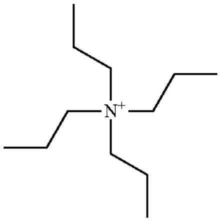

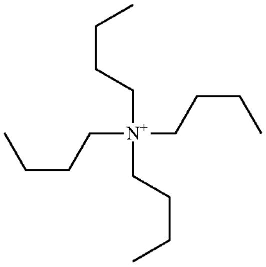

-continued

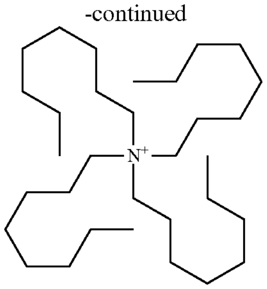

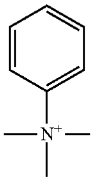

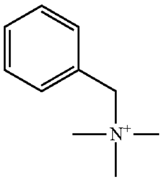

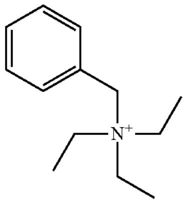

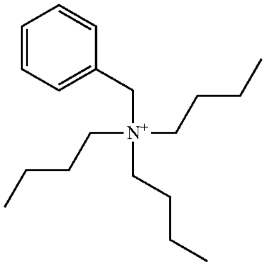

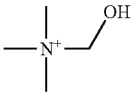

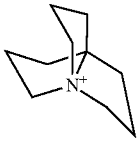

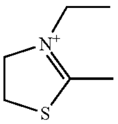

A composition rate of the repeating unit (p-2), which is a repeating unit ratio (p-2), relative to the total of all the repeating units of the polymer compound constituting the inventive resist composition in which the total is 1 satisfies 0<(p-2)≤0.5.

The polymer main chain having the anion structure of the photoacid generator can reduce the acid diffusion and prevent deterioration in the resolution due to blurring with the acid diffusion. In addition, the acid generator is evenly dispersed to improve edge roughness (LER and LWR).

Repeating Unit (a-1)

As a repeating unit (a-1), repeating units same as those described in the above resin (A) can be used.

Repeating Unit (b-1)

As a repeating unit (b-1), repeating units same as those described in the above resin (A) can be used.

Lactone Structure

The resin (B) may have a repeating unit having a lactone structure.

The resin (B), however, may not have a repeating unit having a lactone structure.

The resist composition containing the resin (B) having no lactone structure can inhibit permeating the alkali developer into the pattern to inhibit swelling, and provide a resist pattern having further preferable shape.

<Resin (C)>

The inventive resist composition may further include a resin (C). The resin (C) preferably has no repeating unit changing in its polarity by an action of an acid to be soluble in an alkaline aqueous solution. The resist composition containing the resin (C) can improve uniformity of a film thickness of the resist film on the wafer surface applied by spin-coating.

The resin (C) preferably has a repeating unit represented by the following general formula (c-1), (c-1)

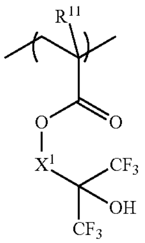

wherein $R^{11}$ represents a hydrogen atom or a methyl group;

$X^1$ represents a single bond or a divalent linking group selected from a divalent hydrocarbon group having 1 to 10 carbon atoms, such as a methylene group, an ethylene group, and a phenylene group, a fluorinated phenylene group, —O—$X^{11}$—, —C(═O)—O—$X^{11}$—, and —C(═O)—NH—$X^{11}$—; and $X^{11}$ represents an alkanediyl group having 1 to 20 carbon atoms and optionally having a carbonyl group, an ester bond, or an ether bond.

Adding such a polymer having the fluoroalcohol structure can improve coating uniformity of the resist film, and can promote the dissolution in the alkaline developer.

Examples of the repeating units represented by the general formula (c-1) include the following repeating units, but the repeating unit is not limited thereto.

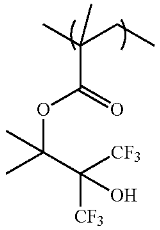

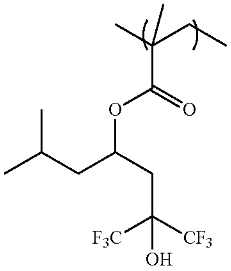

<Onium Salt (E)>

The inventive resist composition may include an onium salt (E) represented by the following general formula (e-1), (e-1)

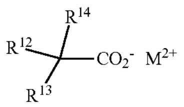

wherein $R^{12}$ and $R^{13}$ each independently represent a hydrogen atom, a fluorine atom, a hydrocarbon group having 1 to 10 carbon atoms and optionally having a fluorine atom, or a trifluoromethyl group;

$R^{14}$ represents a hydrogen atom, a hydroxy group, a substituted or unsubstituted linear alkyl group having 1 to 20 carbon atoms, a substituted or unsubstituted branched or cyclic alkyl group having 3 to 20 carbon atoms, the alkyl group optionally having an ether bond and an ester bond, or a substituted or unsubstituted aryl group having 6 to 30 carbon atoms; and $M^{2+}$ represents a counter cation having a substituent and being a sulfonium cation or an iodonium cation.

Specific examples of the anion structure in the general formula (e-1) include the following structure, but the anion structure is not limited thereto.

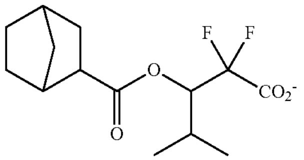

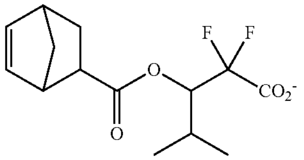

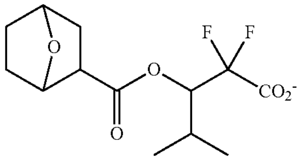

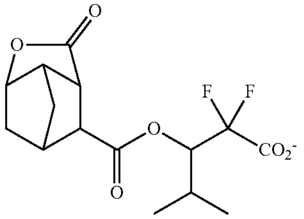

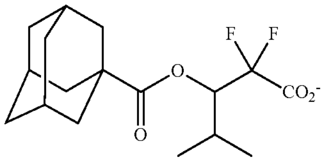

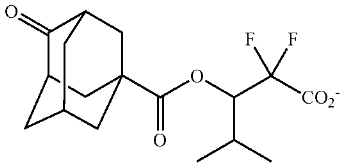

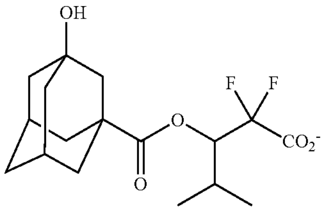

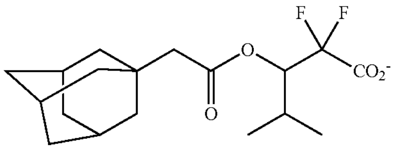

-continued
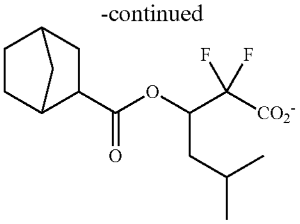
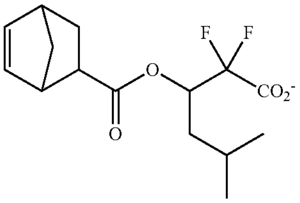
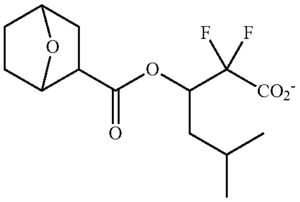
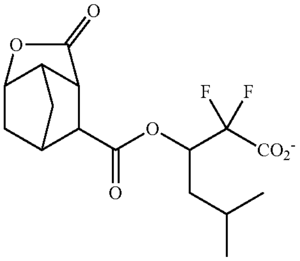
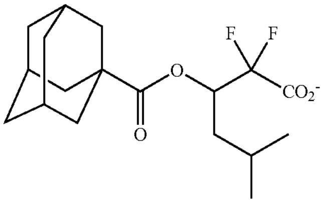
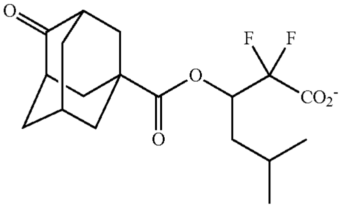
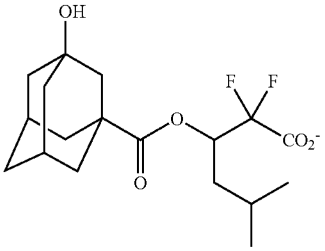
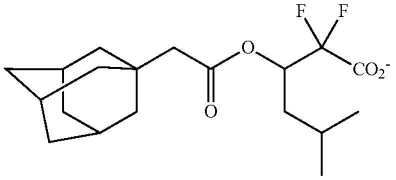
-continued
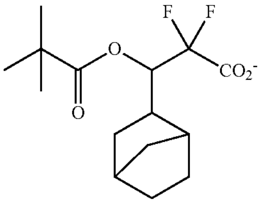
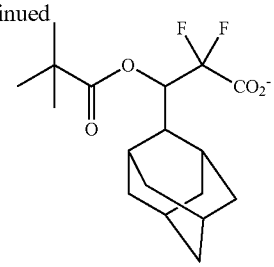
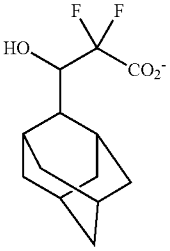
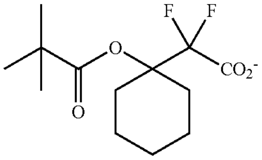
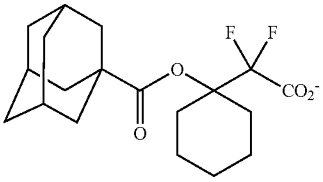
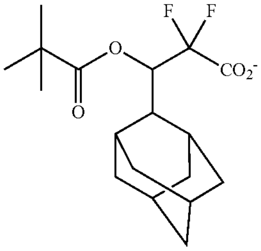
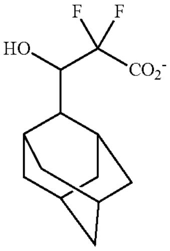
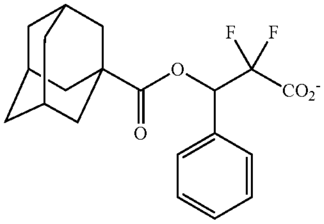
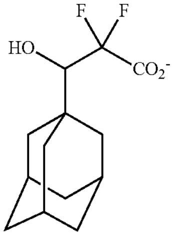
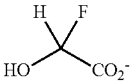
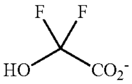
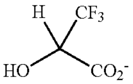
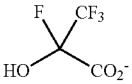
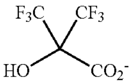
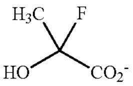
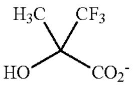
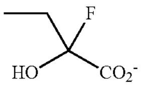
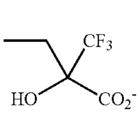
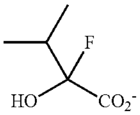
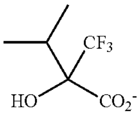

-continued

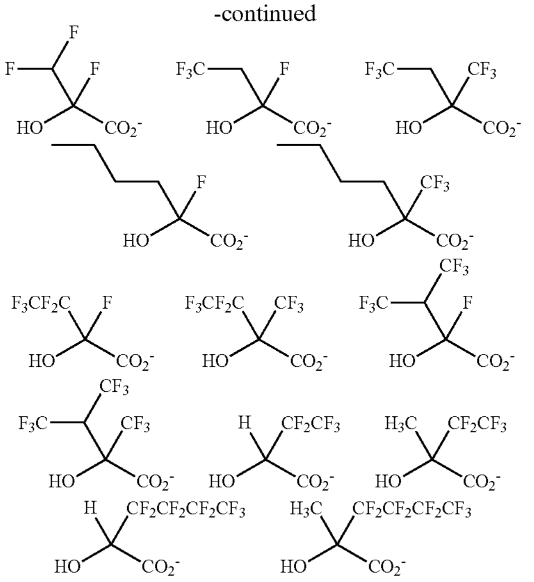

Sulfonium and iodonium cations as the cation structure $M^{2+}$ in the general formula (e-1) can have structures same as of $M^{1+}$, but are not limited thereto.

An amount of the added onium salt (E) is 0 or more and 40 parts by mass or less, preferably 0.1 to 40 parts by mass, and further preferably 0.1 to 20 parts by mass, relative to 100 parts by mass of the total of the resin (A) and the resin (B) in the resist composition. Within the above range, there are no risk of problems of deterioration in resolution and foreign matter after the resist development or during the removal.

A carboxylic acid has lower acid strength than a sulfonium salt to generate an alkanesulfonic acid in which the α-position of the sulfonic acid is substituted with a fluorine atom, and than an alkanesulfonic acid in which the α-position of the sulfonic acid is not substituted with a fluorine atom. Thus, a cation of the carboxylic acid causes salt-exchange with the alkanesulfonic acid in which the α-position of the sulfonic acid is substituted with a fluorine atom contained in a polymer compound such as the polymer compound having the repeating unit (p-2), for example, and the carboxylic acid serves like a quencher. A carboxylic acid having lower acid strength has larger quenching ability and the contrast increases, resulting in excellent rectangular formability and edge roughness of the pattern after the development.

Solvent (D)

The solvent used in the present invention may be any organic solvent that can dissolve the polymer compound, the photoacid generator, the quencher, other additives, etc. Examples of such organic solvents include solvents described in, for example, paragraphs [0144] to [0145] of JP 2008-111103 A, and specifically include: ketones, such as cyclohexanone and methyl-2-n-amylketone; alcohols, such as 3-methoxybutanol, 3-methyl-3-methoxybutanol, 1-methoxy-2-propanol, and 1-ethoxy-2-propanol; ethers, such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters, such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, ethyl 2-hydroxyburyrate, tert-butyl propionate, and propylene glycol mono-tert-butyl ether acetate; lactones, such as γ-butyrolactone; and a mixed solvent thereof. When an acetal-based acid-labile group is used, alcoholic solvents having a high boiling point can be added to promote a deprotection reaction of the acetal. Specific examples of such an alcoholic solvent include diethylene glycol, propylene glycol, glycerin, 1,4-butanediol, and 1,3-butanediol.

Among these organic solvents, preferably used in the present invention are 1-ethoxy-2-propanol, propylene glycol monomethyl ether, propylene glycol dimethyl ether, ethyl lactate, γ-butyrolactone, 4-hydroxy-4-methyl-2-pentanone, and a mixed solvent thereof. These solvents have particularly excellent solubility of the salt-structure-containing polymer in the resist components.

The solvent (D) contained in the inventive resist composition preferably contains a highly polar solvent at a high proportion. Using such a solvent does not decrease the solubility even with mixing the resin (A) and the resin (B), causes no striation during the application, and does not deteriorate the uniformity of the film thickness.

An amount of the organic solvent used in the organic solvent is preferably 200 to 7,000 parts by mass, and particularly preferably 300 to 5,000 parts by mass, relative to 100 parts by mass of the total of the resin (A) and the resin (B).

The solvent contained in the present invention is preferably a mixed solution with a solvent having excellent coatability, such as propylene glycol monomethyl ether acetate and propylene glycol monoethyl ether acetate. As far as the organic solvent is this propylene glycol monomethyl ether acetate (PGMEA), the amount of the used organic solvent is preferably 200 to 4,000 parts by mass, and particularly preferably 300 to 3,000 parts by mass, relative to 100 parts by mass of the total of the resin (A) and the resin (B).

Other Components

The inventive resist composition can include a nitrogen-containing compound as another quencher, a surfactant, etc. as necessary.

(Nitrogen-Containing Compound)

In the present invention, a nitrogen-containing compound can be added as a quencher. Adding this compound can reduce a diffusion rate of the acid generated form the photoacid generator in the resist film. Examples of such a nitrogen-containing compound include primary, secondary, or tertiary amine compounds described in paragraphs [0146] to [0164] of JP 2008-111103 A, and specifically include amine compounds having a hydroxy group, an ether bond, an ester bond, a lactone ring, a cyano group, or a sulfonate ester bond. Examples' thereof also include primary or secondary amines protected as a carbamate group, as compounds described in JP 3790649 B.

These quenchers can be used singly, or can be used in combination of two or more kinds thereof. The blending amount is 0.001 to 12 parts by mass, particularly preferably 0.01 to 8 parts by mass, relative to 100 parts by mass of the base resin. Blending the quencher facilitates to regulation of the resist sensitivity, improves the resolution by inhibiting the diffusion rate of the acid in the resist film, inhibits change in the sensitivity after the exposure, reduces dependency on a substrate or environment, and improves the exposure latitude, pattern profile, etc. Adding these quenchers can also improve substrate adhesiveness.

The inventive resist composition may include a photoacid generator having a nitrogen-containing substituent. Such a compound functions as a so-called photodegradable base, which functions as a quencher in an unexposed portion and losses the quencher ability by neutralization with an acid generated from the compound itself in an exposed portion. Using the photodegradable base can further enhance the contrast between the exposed portion and the unexposed portion. As the photodegradable base, JP 2009-109595 A, JP 2012-46501 A, etc. can be referred, for example.

(Surfactant)

Into the inventive resist composition, a surfactant can be added. Examples of the surfactant include: a surfactant insoluble or hardly soluble in water and soluble in an alkaline developer; and/or a surfactant insoluble or hardly soluble in water and an alkaline developer (hydrophobic resin). As the surfactant, components defined as (S) described in JP 2010-215608 A and JP 2011-16746 A can be referred, for example.

As the surfactant insoluble or hardly soluble in water and an alkaline developer, among the surfactants described in the above publications, FC-4430, SURFLON S-381, SURFYNOL E1004, KH-20, KH-30, and an oxetane ring-opening polymer represented by the following structural formula (surf-1) are preferable. These surfactants can be used singly, or can be used in combination of two or more kinds thereof.

(surf-1)

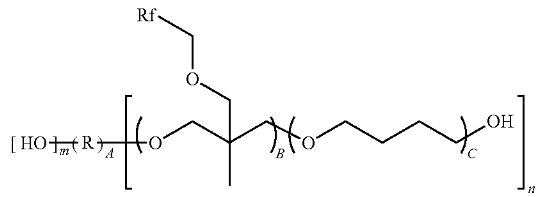

Here, R, Rf, A, B, C, "m", and "n" are applied only in the formula (surf-1) regardless of the above description. R represents a divalent to tetravalent aliphatic group having 2 to 5 carbon atoms. Specific examples of the divalent aliphatic group include ethylene, 1,4-butylene, 1,2-propylene, 2,2-dimethyl-1,3-propylene, and 1,5-pentylene. Specific examples of the trivalent or tetravalent aliphatic group include the following groups.

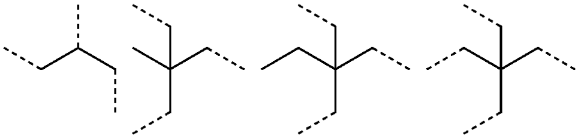

In the formula, a broken line represents a bond. The groups are partial structures derived from glycerol, trimethylolethane, trimethylolpropane, and pentaerythritol, respectively.

Among these, preferably used is 1,4-butylene or 2,2-dimethyl-1,3-propylene. Rf represents a trifluoromethyl group or a pentafluoroethyl group, and preferably represents a trifluoromethyl group. "m" represents an integer of 0 to 3. "n" represents an integer of 1 to 4. A sum of "n" and "m", which represents a valency of R, represents an integer of 2 to 4. A represents 1. B represents an integer of 2 to 25, and C represents an integer of 0 to 10. Preferably, B represents an integer of 4 to 20, and C represents 0 or 1. With each constituting unit in the above structure, the order is not stipulated, and may be block-bonded or random-bonded. Manufacturing of the surfactant of the partially fluorinated oxetane ring-opening polymer is described in detail in U.S. Pat. No. 5,650,483 B.

In the ArF immersion exposure without a resist protective film, the surfactant insoluble or hardly soluble in water and soluble in an alkaline developer has a function of reducing penetration of water or leaching by orientation on the surface of the spin-coated resist film. Thus, such a surfactant is useful for inhibiting elution of a water-soluble component from the resist film to reduce damage of an exposure apparatus. Such a surfactant is also useful because such a surfactant becomes soluble during alkali development after the exposure and the post exposure bake (PEB), and hardly forms a foreign matter causing a defect. Such a surfactant, which has a property of being insoluble or hardly soluble in water and soluble in an alkaline developer, is a polymer-type surfactant and is also referred to as a hydrophobic resin. The surfactant also reduces defects even with dry exposure because the solubility of the surface hardly-soluble layer can be improved. In particular, the surfactant preferably improves the solubility in the alkaline developer. The surfactant also has an effect of improving the film thickness uniformity of the coating film.

The resin (C) is such a polymer-type surfactant, and examples thereof include the following resins.

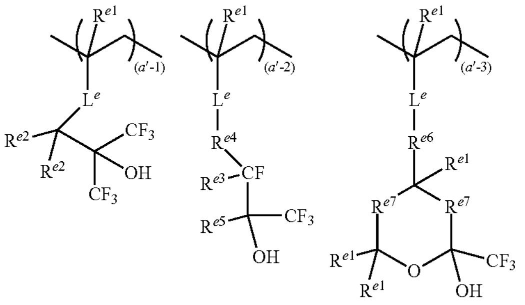

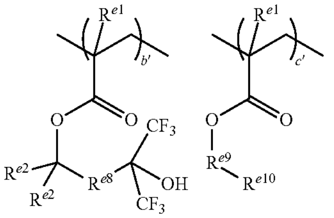

In the formulae, $R^{e1}$ each independently represents a hydrogen atom, a fluorine atom, a methyl group, or a trifluoromethyl group. $R^{e2}$ each independently represents a hydrogen or a linear, branched, or cyclic alkyl group or fluorinated alkyl group having 1 to 20 carbon atoms. $R^{e2}$ in the same repeating unit are optionally bonded each other to form a ring together with the carbon atom to which these $R^{e2}$ are bonded. In this case, these $R^{e2}$ collectively represent a linear, branched, or cyclic alkylene group or fluorinated alkylene group having 2 to 20 carbon atoms.

$R^{e3}$ represents a hydrogen atom or a fluorine atom, or optionally bonded to $R^{e4}$ to form a non-aromatic ring having 3 to 10 carbon atoms together with the carbon atom to which $R^{e3}$ and $R^{e4}$ are bonded. $R^{e4}$ represents a linear, branched, or cyclic alkylene group having 1 to 6 carbon atoms, and one or more hydrogen atoms therein are optionally substituted with a fluorine atom. $R^{e5}$ represents a linear or branched alkyl group having 1 to 10 carbon atoms, and one or more hydrogen atoms therein are substituted with a fluorine atom.

$R^{e4}$ and $R^{e5}$ are optionally bonded to form a non-aromatic ring together with the carbon atom to which $R^{e4}$ and $R^{e5}$ are bonded. In this case, $R^{e4}$, $R^{e5}$, and the carbon atom to which these groups are bonded form a trivalent organic group having 3 to 12 carbon atoms. $R^{e6}$ represents a single bond or an alkylene group having 1 to 4 carbon atoms.

$R^{e7}$ each independently represents a single bond, —O—, or —$CR^{e1}R^{e1}$—. $R^{e8}$ represents a linear or branched alkylene group having 1 to 4 carbon atoms, and optionally bonded to $R^{e2}$ in the same repeating unit to form a non-aromatic ring having 3 to 6 carbon atoms together with the carbon atoms to which $R^{e8}$ and $R^{e2}$.

$R^{e9}$ represents a methylene group, a 1,2-ethylene group, a 1,3-propylene group, or a 1,4-butylene group. $R^{e}10$ represents a linear perfluoroalkyl group having 3 to 6 carbon atoms, a 3H-perfluoropropyl group, a 4H-perfluorobutyl group, a 5H-perfluoropentyl group, or a 6H-perfluorohexyl group.

$L^{e}$ each independently represents —C(=O)—O—, —O—, —O—, or —C(=O)—$R^{e11}$—C(=O)—O—. $R^{e11}$ represents a linear, branched, or cyclic alkylene group having 1 to 10 carbon atoms.

In addition, 0≤(a'-1)≤1, 0≤(a'-2)≤1, 0≤(a'-3)≤1, 0≤b'≤1, and 0≤c'≤1, and 0<(a'-1)+(a'-2)+(a'-3)+b'+c'≤1.

Specific examples of the above repeating unit will be described as follows, but the repeating unit is not limited thereto. In the following formulae, $R^{e1}$ represents the same as above.

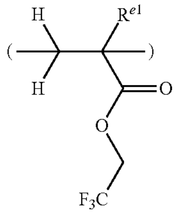

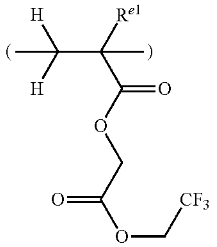

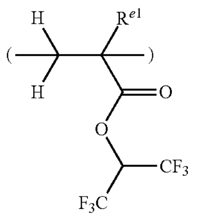

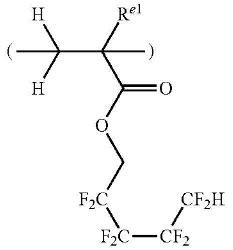

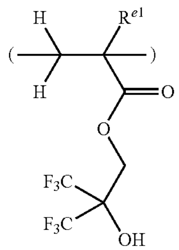

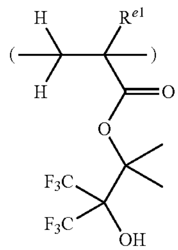

-continued

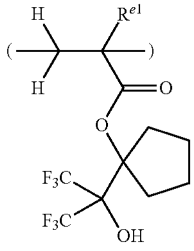

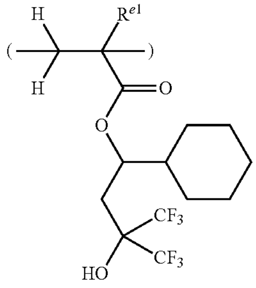

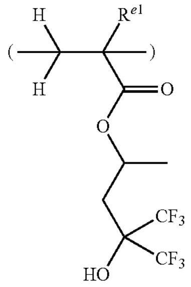

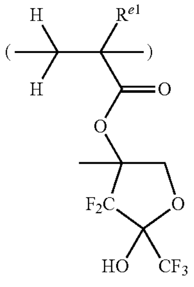

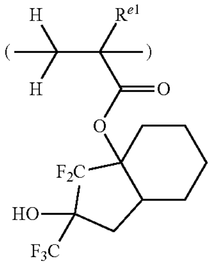

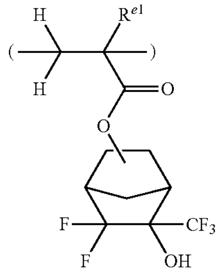

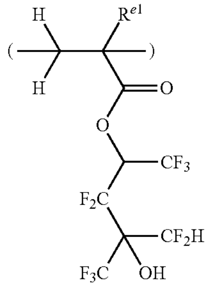

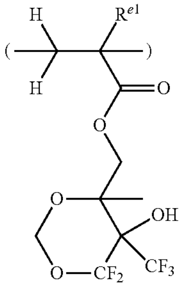

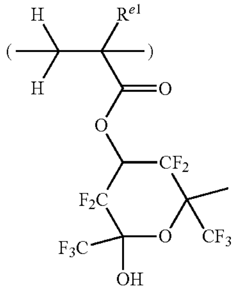

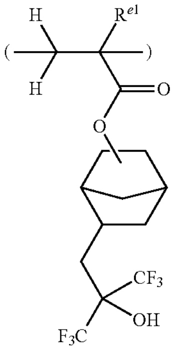

-continued

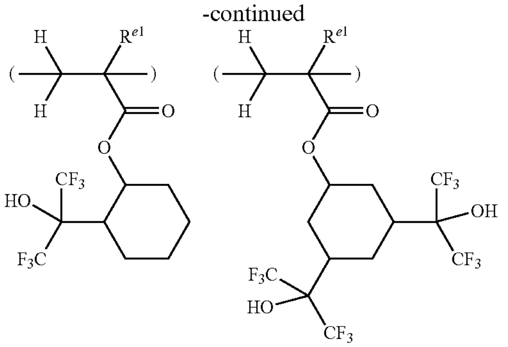

The polymer-type surfactant preferably has Mw of 1,000 to 50,000, more preferably 2,000 to 20,000. Within this range, the effect of surface modification is sufficient, and development defect hardly occurs.

For the surfactant insoluble or hardly soluble in water and soluble in an alkaline developer, JP 2008-122932 A, JP 2010-134012 A, JP 2010-107695 A, JP 2009-276363 A, JP 2009-192784 A, JP 2009-191151 A, JP 2009-98638 A, JP 2010-250105 A, and JP 2011-42789 A can also be referred.

A blending amount of the surfactant is 0 to 20 parts by mass relative to 100 parts by mass of the resist solid content. When the surfactant is blended, a lower limit thereof is preferably 0.001 part by mass, and more preferably 1 part by mass. An upper limit thereof is preferably 15 parts by mass, and more preferably 5 parts by mass.

Patterning Process

The present invention further provides a patterning process including: forming a resist film on a substrate by using the aforementioned resist composition, holding a mask over the resist film; irradiating a high-energy ray to expose the resist film; and then developing the resist film with an alkaline developer to form a pattern on the substrate.

The patterning process includes:

(i) a step of forming a resist film on a substrate by using the inventive resist composition;

(ii) a step of exposing the resist film to KrF excimer laser with a wavelength of 248 nm, ArF excimer laser with a wavelength of 193 nm, EUV lithography with a wavelength of 13.5 nm, or electron beam; and (iii) a step of developing the exposed resist film with an alkaline developer.

For forming a pattern using the inventive resist composition, known lithography technology can be applied. For example, on a substrate for integrated circuit manufacturing (such as Si, $SiO_2$, SiN, SiON, TiN, WSi, BPSG, SOG, and an organic anti-reflective film) or a substrate for mask circuit manufacturing (such as Cr, CrO, CrON, and MoSi), the resist composition is applied by a method such as spin-coating so that the film thickness is 0.05 to 2.0 μm. This film is pre-baked on a hot plate at 60 to 150° C. for 1 to 10 minutes, preferably at 80 to 140° C. for 1 to 5 minutes. Then, a mask for forming a target pattern is held over the above resist film, and the high-energy ray such as KrF excimer laser, ArF excimer laser, and EUV is irradiated so that the exposure dose is 1 to 200 mJ/$cm^2$, preferably 10 to 100 mJ/$cm^2$. The exposure can be performed by using, other than the common exposure method, an immersion method of immersing the gap between the mask and the resist film in some cases. In this case, a water-insoluble protective film can be used. Then, the exposed film is subjected to post exposure bake (PEB) on a hot plate at 60 to 150° C. for 1 to 5 minutes, preferably at 80 to 140° C. for 1 to 3 minutes.

Furthermore, the development is performed using a developer of a 0.1 to 5 mass %, preferably 2 to 3 mass %, alkaline aqueous solution of tetramethylammonium hydroxide (TMAH), etc. for 0.1 to 3 minutes, preferably 0.5 to 2 minutes, by a common method such as a dip method, a puddle method, and a spray method to form a target pattern on the substrate.

For the developer in the inventive patterning process, as described above, a developer of a 0.1 to 5 mass %, preferably 2 to 3 mass %, alkaline aqueous solution of tetramethylammonium hydroxide (TMAH), etc. can be used.

EXAMPLE

Hereinafter, the present invention will be specifically described with showing Examples and Comparative Examples, but the present invention is not limited by these descriptions.

A structure of each repeating unit is shown below.

(p-1) Unit

P1-1

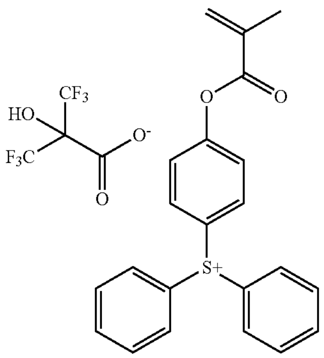

P1-2

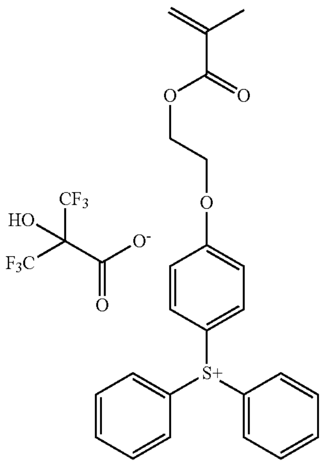

-continued
P1-3
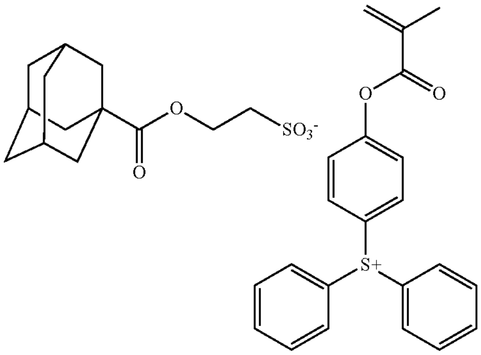
P1-4
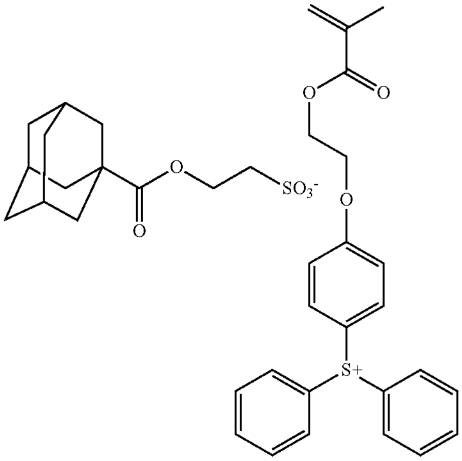
P1-5
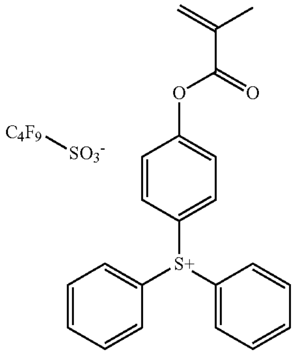
(p-2) Unit
P2-1
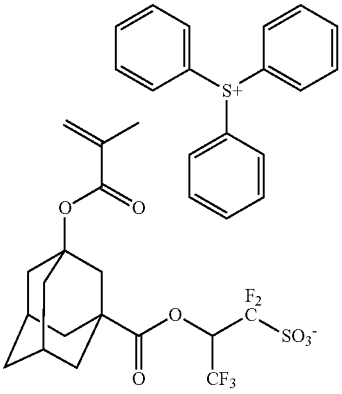
-continued
P2-2
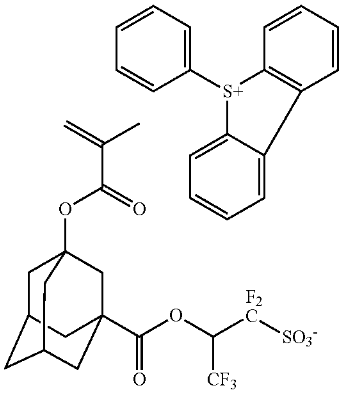
P2-3
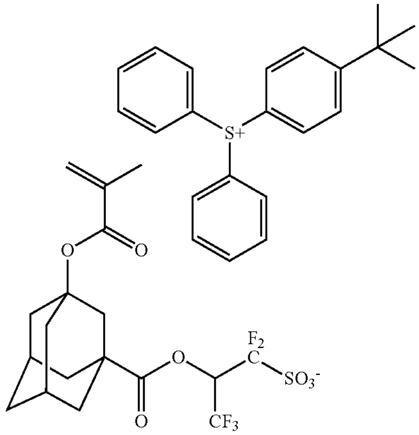
P2-4
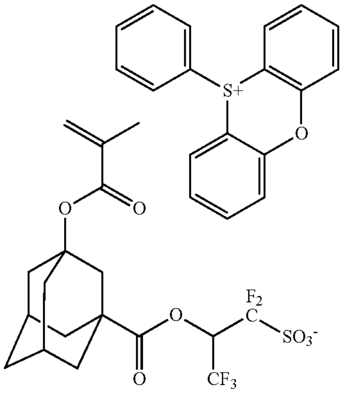
P2-5
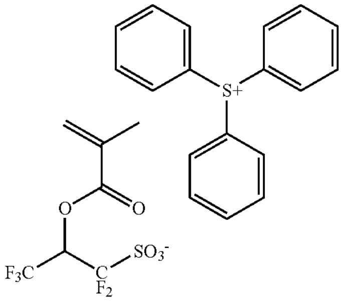

-continued
P2-6
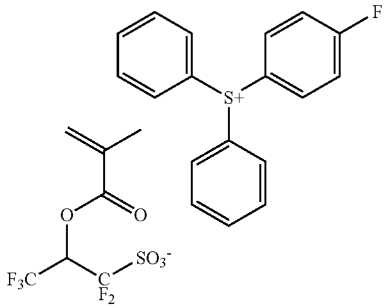
P2-7
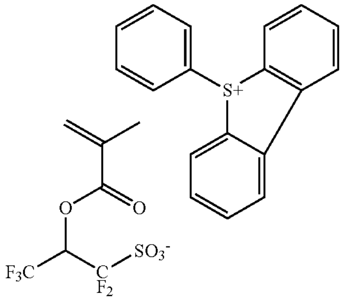
(a-1) Unit
A-1
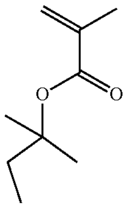
A-2
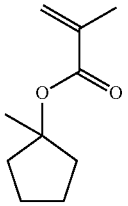
A-3
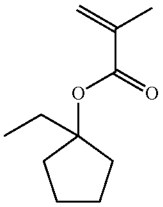
A-4
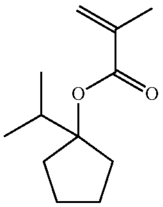
-continued
A-5
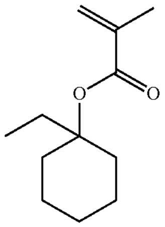
A-6
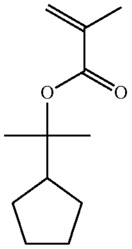
A-7
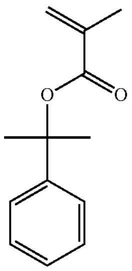
A-8
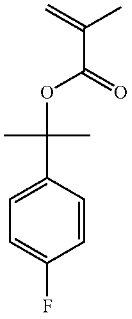
(b-1) Unit
B-1
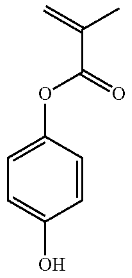

-continued

B-2

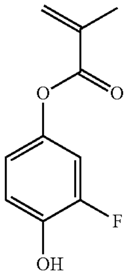

B-3

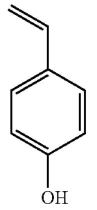

B-4

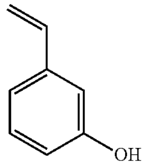

Lactone Unit

F-1

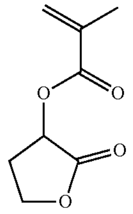

F-2

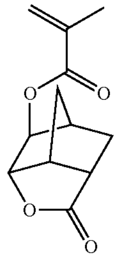

Polymer Synthesis Example 1

Polymer Synthesis Example: PA-1

Under a nitrogen atmosphere, 6.6 g of the monomer P1-1, 7.0 g of the monomer A-1, 6.4 g of the monomer B-1, 0.24 g of V-601 (Dimethyl 2,2'-azobis(2-methylpropionate; manufactured by Wako Pure Chemical Industries, Ltd.), 0.2 g of 2-mercaptoethanol, and 25 g of methyl ethyl ketone were added into a flask to prepare a monomer-polymerization initiator solution. Into another flask with a nitrogen atmosphere, 23 g of methyl ethyl ketone was added to be heated to 80° C. with stirring, and then the monomer-polymerization initiator solution was added dropwise over 4 hours at the temperature. After the dropwise addition, the polymerization liquid was further stirred for 2 hours with maintaining the temperature at 80° C., and then cooled to a room temperature. The obtained polymerization liquid was added dropwise to 400 g of vigorously stirred hexane, and a precipitated polymer was filtered. The polymer was washed twice with 120 g of hexane, and then dried in vacuo at 50° C. for 20 hours to obtain 18 g of a white powder polymer PA-1.

Polymer Synthesis Example 2

(Polymer Synthesis Examples: PA-2 to PA-21, PB-1 to PB-15, P-1, and P-2)

In the same procedure as in Polymer Synthesis Example PA-1, polymers PA-2 to PA-21, polymers PB-1 to PB-15, P-1, and P-2 were synthesized at a monomer composition and introduction rate, mole fraction, shown in Tables 1 and 2.

TABLE 1

| Resin | Unit 1 (introduction rate) | | Unit 2 (introduction rate) | | Unit 3 (introduction rate) | | Unit 4 (introduction rate) | |
|---|---|---|---|---|---|---|---|---|
| PA-1 | P1-1 | 0.1 | A-1 | 0.5 | B-1 | 0.4 | | |
| PA-2 | P1-1 | 0.05 | A-1 | 0.6 | B-2 | 0.35 | | |
| PA-3 | P1-1 | 0.1 | A-1 | 0.55 | B-3 | 0.35 | | |
| PA-4 | P1-1 | 0.1 | A-1 | 0.6 | B-4 | 0.3 | | |
| PA-5 | P1-1 | 0.05 | A-2 | 0.6 | B-1 | 0.35 | | |
| PA-6 | P1-1 | 0.1 | A-3 | 0.5 | B-4 | 0.4 | | |
| PA-7 | P1-1 | 0.1 | A-4 | 0.5 | B-1 | 0.4 | | |
| PA-8 | P1-1 | 0.15 | A-1 | 0.5 | B-1 | 0.25 | F-1 | 0.1 |
| PA-9 | P1-2 | 0.05 | A-1 | 0.5 | B-1 | 0.45 | | |
| PA-10 | P1-2 | 0.05 | A-2 | 0.55 | B-4 | 0.4 | | |
| PA-11 | P1-2 | 0.05 | A-3 | 0.55 | B-1 | 0.4 | | |
| PA-12 | P1-3 | 0.05 | A-7 | 0.6 | B-3 | 0.35 | | |
| PA-13 | P1-3 | 0.15 | A-8 | 0.5 | B-1 | 0.35 | | |
| PA-14 | P1-3 | 0.05 | A-1 | 0.7 | B-1 | 0.25 | | |
| PA-15 | P1-3 | 0.1 | A-5 | 0.5 | B-3 | 0.4 | | |
| PA-16 | P1-3 | 0.05 | A-6 | 0.6 | B-4 | 0.35 | | |
| PA-17 | P1-3 | 0.05 | A-2 | 0.45 | B-2 | 0.3 | F-2 | 0.2 |
| PA-18 | P1-4 | 0.15 | A-8 | 0.5 | B-4 | 0.35 | | |
| PA-19 | P1-4 | 0.1 | A-4 | 0.6 | B-3 | 0.3 | | |
| PA-20 | P1-5 | 0.1 | A-7 | 0.5 | B-3 | 0.4 | | |
| PA-21 | P1-5 | 0.1 | A-2 | 0.55 | B-4 | 0.35 | | |

TABLE 2

| Resin | Unit 1 (introduction rate) | | Unit 2 (introduction rate) | | Unit 3 (introduction rate) | | Unit 4 (introduction rate) | |
|---|---|---|---|---|---|---|---|---|
| PB-1 | P2-1 | 0.1 | A-1 | 0.5 | B-1 | 0.4 | | |
| PB-2 | P2-1 | 0.15 | A-3 | 0.5 | B-3 | 0.35 | | |
| PB-3 | P2-1 | 0.2 | A-5 | 0.5 | B-3 | 0.3 | | |
| PB-4 | P2-1 | 0.1 | A-7 | 0.55 | B-4 | 0.35 | | |
| PB-5 | P2-2 | 0.15 | A-2 | 0.5 | B-4 | 0.35 | | |
| PB-6 | P2-2 | 0.25 | A-6 | 0.45 | B-1 | 0.3 | | |
| PB-7 | P2-2 | 0.25 | A-8 | 0.5 | B-4 | 0.25 | | |
| PB-8 | P2-2 | 0.15 | A-7 | 0.55 | B-3 | 0.3 | | |
| PB-9 | P2-3 | 0.15 | A-3 | 0.6 | B-2 | 0.25 | | |
| PB-10 | P2-3 | 0.15 | A-7 | 0.55 | B-1 | 0.3 | | |
| PB-11 | P2-4 | 0.15 | A-6 | 0.4 | B-1 | 0.3 | F-1 | 0.15 |
| PB-12 | P2-5 | 0.1 | A-7 | 0.5 | B-1 | 0.4 | | |
| PB-13 | P2-5 | 0.1 | A-3 | 0.6 | B-1 | 0.3 | | |
| PB-14 | P2-6 | 0.1 | A-5 | 0.55 | B-4 | 0.35 | | |
| PB-15 | P2-7 | 0.1 | A-5 | 0.4 | B-3 | 0.35 | F-2 | 0.15 |
| P-1 | | | A-4 | 0.60 | B-3 | 0.25 | F-1 | 0.15 |
| P-2 | | | A-3 | 0.60 | B-1 | 0.40 | | |

Preparation of Resist Composition

The resins (A) are represented by the polymers PA-1 to 21, and the resins (B) are represented by the polymers PB-1 to 15. The resin (A) and the resin (B) were mixed. Relative to a total of the addition amounts of the resin (A) and the resin (B) in this time being 100 parts by mass, addition amounts of a solvent (D), a resin (C), and additives (an onium salt 1, an onium salt 2, and a nitrogen-containing compound) are shown as parts by mass in Tables 3 and 4. As a surfactant, a surfactant FC-4430, manufactured by Sumitomo 3M Limited., was dissolved at 100 ppm, and the dissolved solution was filtered with a filter made of Teflon® (pore diameter: 0.2 μm) to prepare a resist composition shown in the following Tables 3 and 4.

The solvents shown in Tables 3 to 5 are as follows.

PGMEA: Propylene glycol monomethyl ether acetate

PGME: Propylene glycol monomethyl ether

EL: Ethyl lactate

HBM: 4-Hydroxy-4-methyl-2-pentanone

GBL: γ-Butyrolactone

SF-1

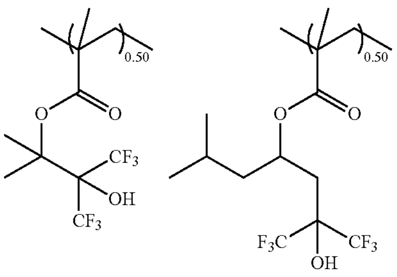

SF-2

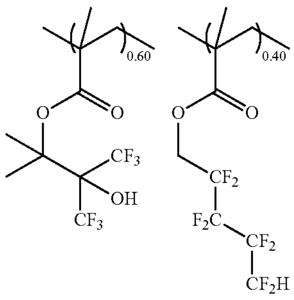

SF-3

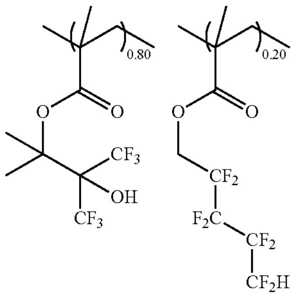

Compositions of the onium salt 1, onium salt 2, and nitrogen-containing compound are as shown below.

Onium Salt 1

PDQ-1

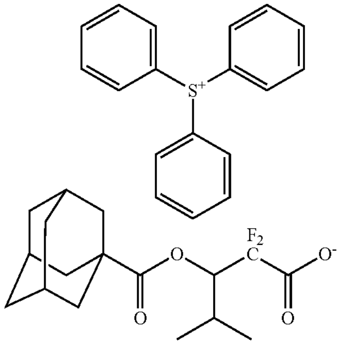

PDQ-2

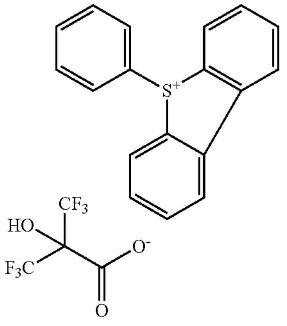

PDQ-3

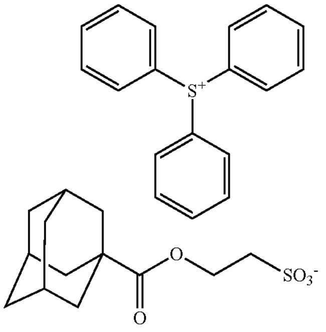

PDQ-4

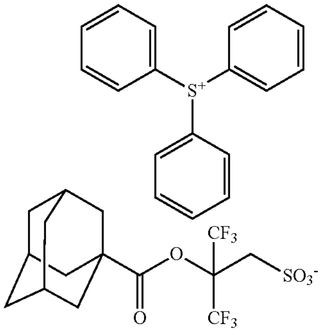

-continued

Onium Salt 2

PAG-1

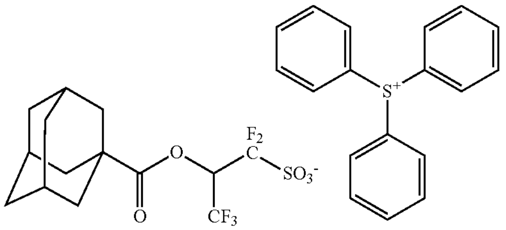

PAG-2

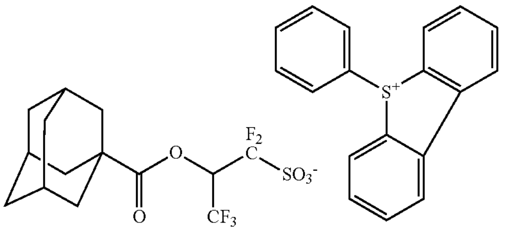

Nitrogen-Containing Compound

AQ-1

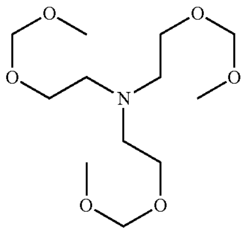

AQ-2

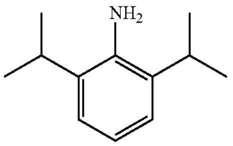

TABLE 3

| Resist | Resin (A) (parts by mass) | | Resin (B) (parts by mass) | | Resin (C) (parts by mass) | | Additive (parts by mass ) | | Solvent (parts by mass) | |
|---|---|---|---|---|---|---|---|---|---|---|
| R-1 | PA-1 | 25 | PB-1 | 75 | SF-1 | 5 | PDQ-1 | 5.7 | PGMEA | 1000 |
| | | | | | | | | | PGME | 3000 |
| | | | | | | | | | GBL | 1000 |
| R-2 | PA-1 | 40 | PB-1 | 60 | SF-2 | 5 | | | PGMEA | 1250 |
| | | | | | | | | | PGME | 3000 |
| | | | | | | | | | GBL | 750 |
| R-3 | PA-1 | 40 | PB-2 | 60 | | | PDQ-2 | 6.0 | PGMEA | 1250 |
| | | | | | | | | | EL | 3000 |
| | | | | | | | | | GBL | 750 |
| R-4 | PA-1 | 40 | PB-3 | 60 | SF-3 | 5 | | | PGMEA | 1000 |
| | | | | | | | | | PGME | 3000 |
| | | | | | | | | | HBM | 1000 |
| R-5 | PA-2 | 40 | PB-6 | 60 | | | | | PGMEA | 1000 |
| | | | | | | | | | PGME | 3000 |
| | | | | | | | | | EL | 1000 |
| R-6 | PA-3 | 40 | PB-4 | 60 | SF-3 | 5 | PDQ-2 | 5.7 | PGMEA | 1000 |
| | | | | | | | | | PGME | 3000 |
| | | | | | | | | | HBM | 1000 |
| R-7 | PA-4 | 40 | PB-5 | 60 | SF-3 | 5 | PDQ-2 | 4.2 | PGMEA | 1000 |
| | | | | | | | | | PGME | 3000 |
| | | | | | | | | | GBL | 1000 |
| R-8 | PA-5 | 30 | PB-7 | 70 | SF-3 | 5 | | | PGMEA | 1000 |
| | | | | | | | | | PGME | 3000 |
| | | | | | | | | | EL | 1000 |
| R-9 | PA-6 | 40 | PB-10 | 60 | SF-3 | 5 | PDQ-2 | 3.3 | PGMEA | 1000 |
| | | | | | | | | | PGME | 3000 |
| | | | | | | | | | HBM | 1000 |
| R-10 | PA-7 | 40 | PB-12 | 60 | SF-3 | 5 | | | PGMEA | 1250 |
| | | | | | | | | | PGME | 3000 |
| | | | | | | | | | GBL | 750 |
| R-11 | PA-13 | 40 | PB-1 | 60 | | | PAG-1 | 4.0 | PGMEA | 1250 |
| | | | | | | | PDQ-2 | 6.6 | PGME | 3000 |
| | | | | | | | | | GBL | 750 |
| R-12 | PA-16 | 30 | PB-5 | 70 | SF-3 | 5 | PDQ-1 | 4.3 | PGMEA | 1000 |
| | | | | | | | | | PGME | 3000 |
| | | | | | | | | | GBL | 1000 |
| R-13 | PA-9 | 40 | PB-9 | 60 | SF-3 | 5 | AQ-1 | 3.0 | PGMEA | 1000 |
| | | | | | | | | | PGME | 3000 |
| | | | | | | | | | HBM | 1000 |
| R-14 | PA-10 | 30 | PB-10 | 70 | | | PDQ-4 | 4.5 | PGMEA | 1000 |
| | | | | | | | | | PGME | 3000 |
| | | | | | | | | | EL | 1000 |
| R-15 | PA-15 | 40 | PB-13 | 60 | | | | | PGMEA | 1000 |
| | | | | | | | | | PGME | 3000 |
| | | | | | | | | | HBM | 1000 |
| R-16 | PA-21 | 40 | PB-14 | 60 | SF-3 | 5 | PDQ-3 | 4.5 | PGMEA | 1250 |
| | | | | | | | | | PGME | 3000 |
| | | | | | | | | | GBL | 750 |

TABLE 4

| Resist | Resin (A) (parts by mass ) | | Resin (B) (parts by mass ) | | Resin (C) (parts by mass) | | Additive by (parts mass) | | Solvent (parts by mass) | |
|---|---|---|---|---|---|---|---|---|---|---|
| R-17 | PA-12 | 30 | PB-4 | 70 | SF-1 | 5 | PDQ-1 | 5.7 | PGMEA | 1000 |
| | | | | | | | | | PGME | 3000 |
| | | | | | | | | | EL | 1000 |
| R-18 | PA-11 | 40 | PB-11 | 60 | SF-3 | 5 | | | PGMEA | 1000 |
| | | | | | | | | | PGME | 3000 |
| | | | | | | | | | HBM | 1000 |
| R-19 | PA-8 | 30 | PB-8 | 70 | SF-3 | 5 | PDQ-2 | 6.8 | PGMEA | 1000 |
| | | | | | | | | | PGME | 3000 |
| | | | | | | | | | EL | 1000 |
| R-20 | PA-17 | 40 | PB-15 | 60 | SF-2 | 5 | | | PGMEA | 1000 |
| | | | | | | | | | PGME | 3000 |
| | | | | | | | | | GBL | 1000 |
| R-21 | PA-20 | 40 | PB-15 | 60 | SF-3 | 5 | PDQ-1 | 6.2 | PGMEA | 1000 |
| | | | | | | | | | PGME | 3000 |
| | | | | | | | | | GBL | 1000 |
| R-22 | PA-18 | 25 | PB-5 | 75 | SF-1 | 5 | PDQ-1 | 4.3 | PGMEA | 1250 |
| | | | | | | | | | PGME | 3000 |
| | | | | | | | | | GBL | 750 |
| R-23 | PA-21 | 40 | PB-14 | 60 | SF-3 | 5 | PDQ-3 | 4.5 | PGMEA | 1250 |
| | | | | | | | | | PGME | 3000 |
| | | | | | | | | | GBL | 750 |
| R-24 | PA-2 | 60 | PB-2 | 40 | | | PAG-2 | 4.0 | PGMEA | 1000 |
| | | | | | | | PDQ-3 | 6.6 | PGME | 3000 |
| | | | | | | | | | GBL | 1000 |
| R-25 | PA-14 | 60 | PB-1 | 40 | SF-1 | 5 | PDQ-1 | 5.7 | PGMEA | 1000 |
| | | | | | | | | | PGME | 3000 |
| | | | | | | | | | GBL | 1000 |
| R-26 | PA-1 | 100 | | | SF-3 | 5 | PAG-1 | 35 | PGMEA | 1500 |
| | | | | | | | | | PGME | 3500 |
| R-27 | PA-19 | 100 | | | | | PAG-2 | 25 | PGMEA | 4000 |
| | | | | | | | AQ-2 | 2.2 | GBL | 1000 |
| R-28 | | | PB-2 | 100 | | | AQ-1 | 3.6 | PGMEA | 3000 |
| | | | | | | | | | PGME | 1000 |
| | | | | | | | | | EL | 1000 |

TABLE 4-continued

| Resist | Resin (A) (parts by mass) | | Resin (B) (parts by mass) | | Resin (C) (parts by mass) | | Additive by (parts mass) | | Solvent (parts by mass) | |
|---|---|---|---|---|---|---|---|---|---|---|
| R-29 | | | PB-2 | 100 | SF-2 | 5 | PDQ-3 | 4.6 | PGMEA<br>PGME<br>HBM | 2000<br>2000<br>1000 |
| R-30 | P-1 | 25 | PB-1 | 75 | | | PDQ-1 | 6.5 | PGMEA<br>GBL | 4000<br>1000 |
| R-31 | PA-1 | 50 | P-2 | 50 | SF-1 | 5 | PAG-1 | 12.0 | PGMEA<br>GBL | 4000<br>1000 |
| R-32 | P-1 | 100 | | | | | PAG-1<br>PDQ-2 | 16.0<br>4.0 | PGMEA<br>GBL | 4500<br>500 |

Evaluation of DLS Particle Diameter by Dynamic Light Scattering

The dynamic light scattering is referred to as DLS hereinafter. A polymer solution having a regulated concentration of 1.5 wt % was subjected to DLS using a device DynaPro NanoSter (manufactured by Wyatt Technology Corporation) to measure a DLS particle diameter. In the present invention, the polymers PA-6 and PB-5, and a mixed liquid thereof were measured under the condition shown in the following Table. It is expected to confirm that mixing the polymers increases the DLS particle diameter compared with the polymer alone, and forms a polymer composite.

TABLE 5

| Resin solution | Resin (A) (parts by mass ) | Resin (B) (parts by mass) | Solvent (parts by mass) | | DLS particle diameter (nm) |
|---|---|---|---|---|---|
| Sol-12 | PA-6 (100) | — | PGMEA<br>PGME<br>GBL | 1250<br>3000<br>750 | 1.9 |
| Sol-13 | — | PB-5 (100) | PGMEA<br>PGME<br>GBL | 1250<br>3000<br>750 | 2.0 |
| Sol-14 | PA-6 (20) | PB-5 (80) | PGMEA<br>PGME<br>GBL | 1250<br>3000<br>750 | 2.6 |
| Sol-15 | PA-6 (40) | PB-5 (60) | PGMEA<br>PGME<br>GBL | 1250<br>3000<br>750 | 2.9 |

Evaluation of EUV Exposure Patterning (Line Pattern Evaluation)

An organic anti-reflective film AL-412, manufactured by BREWER SCIENCE Inc., was formed with a film thickness of 20 nm on a substrate. The inventive resist compositions (R-1 to R-23) and the comparative resist compositions (R-24 to R-32) were each applied on the coated substrate by using CLEAN TRACK Lithius ProZ, manufactured by Tokyo Electron Ltd. The composition was baked on a hot plate at 105° C. for 60 seconds to form a resist film with 50 nm. Using an EUV exposure device NXE 3400, manufactured by ASML Holding N.V., the resist film was exposed with a pattern with 40 nm in pitch and 20 nm in line-and-space of a size on mask. After the exposure, PEB was performed at a temperature that was appropriate for each resist composition, and then developed for a total of 30 seconds with discharging a 2.38% aqueous solution of tetramethyl ammonium on the substrate rotating. The alkaline solution was washed out with water, and the wafer was rotated at a high speed to remove the water.

(Sensitivity Evaluation)

The produced resist pattern was observed with CD-SEM CG-6300, manufactured by Hitachi High-Technologies Corporation. An exposure dose that yielded a line pattern being 20 nm with 40 nm in pitch was specified as an optimum exposure dose Eop ($mJ/cm^2$).

(Evaluation of Line Width Roughness (LWR))

The obtained hole pattern was observed with CD-SEM CG-6300, manufactured by Hitachi High-Technologies Corporation., to measure lengths of 32 CD widths per line. From one SEM image, 11 line widths were measured to specify the variation of the CD widths as LWR. A smaller value of LWR means more excellent size uniformity. An LWR of 3.0 or less was judged as "Good".

On the inventive resist compositions, the resist coatability was also evaluated in the same evaluation method as of the polymer solution. "Range" of 10 Å or more was judged as "Poor", "Range" of 10 to 5 Å was judged as "Fair", and "Range" of 5 Å or less was judged as "Good". Tables 6 and 7 show the results.

Evaluation of Coatability of Resist Composition

Using the prepared resist composition, coatability on a silicon wafer substrate was determined. The resist composition was applied on a silicon wafer substrate with 300 mm by using CLEAN TRACK Lithius ProAP, manufactured by Tokyo Electron Ltd. The composition was baked on a hot plate at 105° C. for 60 seconds to form a resist film with 50 nm. The film thickness was measured by using a light-interference film thickness meter VM3210, manufactured by SCREEN Semiconductor Solutions Co., Ltd. A difference between a maximum film thickness and a minimum film thickness among 11 measured points was specified as "Range" (Å). "Range" of 10 Å or more was judged as "Poor", "Range" of 10 to 5 Å was judged as "Fair", and "Range" of 5 Å or less was judged as "Good". Tables 6 and 7 show the results.

TABLE 6

| Example | Resist composition | PEB (° C.) | Eop ($mJ/cm^2$) | LWR (nm) | Coatability |
|---|---|---|---|---|---|
| Example 1 | R-1 | 90 | 70 | 2.3 | Good |
| Example 2 | R-2 | 85 | 79 | 2.5 | Good |
| Example 3 | R-3 | 95 | 72 | 2.3 | Fair |
| Example 4 | R-4 | 95 | 65 | 2.5 | Good |
| Example 5 | R-5 | 100 | 55 | 2.6 | Fair |
| Example 6 | R-6 | 90 | 74 | 2.4 | Good |
| Example 7 | R-7 | 95 | 68 | 2.3 | Good |
| Example 8 | R-8 | 95 | 51 | 2.7 | Good |
| Example 9 | R-9 | 95 | 88 | 2.8 | Good |
| Example 10 | R-10 | 100 | 65 | 2.6 | Good |
| Example 11 | R-11 | 100 | 73 | 2.7 | Fair |
| Example 12 | R-12 | 95 | 60 | 2.3 | Good |
| Example 13 | R-13 | 95 | 64 | 2.9 | Good |
| Example 14 | R-14 | 100 | 92 | 2.9 | Fair |
| Example 15 | R-15 | 95 | 51 | 2.6 | Fair |
| Example 16 | R-16 | 100 | 88 | 2.8 | Fair |
| Example 17 | R-17 | 85 | 46 | 2.7 | Good |
| Example 18 | R-18 | 100 | 86 | 2.9 | Good |
| Example 19 | R-19 | 100 | 77 | 2.6 | Good |
| Example 20 | R-20 | 100 | 70 | 2.7 | Good |
| Example 21 | R-21 | 95 | 80 | 2.9 | Good |
| Example 22 | R-22 | 100 | 45 | 2.9 | Good |
| Example 23 | R-23 | 100 | 108 | 2.8 | Good |

TABLE 7

| Example | Resist composition | PEB (° C.) | Eop ($mJ/cm^2$) | LWR (nm) | Coatability |
|---|---|---|---|---|---|
| Comparative Example 1 | R-24 | 90 | 94 | 3.1 | Fair |
| Comparative Example 2 | R-25 | 90 | 107 | 3.5 | Good |
| Comparative Example 3 | R-26 | 95 | 58 | 3.3 | Good |

TABLE 7-continued

| Example | Resist composition | PEB (° C.) | Eop (mJ/cm$^2$) | LWR (nm) | Coatability |
|---|---|---|---|---|---|
| Comparative Example 4 | R-27 | 100 | 66 | 3.9 | Good |
| Comparative Example 5 | R-28 | 105 | 37 | 3.3 | Fair |
| Comparative Example 6 | R-29 | 90 | 33 | 3.1 | Good |
| Comparative Example 7 | R-30 | 95 | 46 | 3.5 | Good |
| Comparative Example 8 | R-31 | 100 | 77 | 3.3 | Good |
| Comparative Example 9 | R-32 | 95 | 68 | 3.6 | Good |

From the results shown in Tables 6 and 7, the inventive resist compositions (Examples 1 to 23) exhibited good LWR of 3.0 or less. Meanwhile, Comparative Examples 1 to 9 exhibited LWR over 3.0.

Among Comparative Examples (Comparative Examples 1 to 9), when the amount of the resin (A) was larger than the amount of the resin (B) and a large amount of the resin (A) is present in the resist solid content, such as Comparative Examples 1 to 4 for example, an amount of the strong acid component is small to have poor reactivity of the acid leaving group, resulting in failure to satisfy the numerical range of LWR of 3.0 or less.

In contrast, when a large amount of the resin (B) is present in the resist solid content, such as Comparative Examples 5 and 6, the exposed portion easily attracted the alkaline developer, which was found from the small DLS particle diameter of the resin (B) in Table 5. Thus, a variation on the pattern boundary became large to fail to satisfy the numerical range of LWR of 3.0 or less.

The inventive resist composition has been demonstrated to be useful for the alkaline aqueous solution development process because the resin (A) and the resin (B) are mixed so that the resin (A) is less than the resin (B) to form a polymer composite, and a pattern having excellent LWR can be formed even with a high exposure region.

From the results in Tables 6 and 7, the inventive resist composition containing the resin (C) has been demonstrated to have excellent coatability.

From the above results, it has been demonstrated that the inventive resist composition can form a resist film having reduced LWR. Therefore, it has been demonstrated that the present invention can provide a resist composition that reduces roughness (LER and LWR) and size uniformity (CDU) of a hole pattern with high resolution exceeding that of conventional resist materials, that has good pattern shape after the exposure, and that has excellent etching resistance.

It should be noted that the present invention is not limited to the above-described embodiments. The embodiments are just examples, and any examples that substantially have the same feature and demonstrate the same functions and effects as those in the technical concept disclosed in claims of the present invention are included in the technical scope of the present invention.

The invention claimed is:

1. A resist composition, comprising:

a resin (A) having: a repeating unit represented by the following general formula (p-1); a repeating unit represented by the following general formula (a-1) and changing in its polarity by an action of an acid to be soluble in an alkaline aqueous solution; and a repeating unit represented by the following general formula (b-1);

a resin (B) having: a repeating unit represented by the following general formula (p-2); a repeating unit represented by the following general formula (a-1) and changing in its polarity by an action of an acid to be soluble in an alkaline aqueous solution; and a repeating unit represented by the following general formula (b-1); and a solvent (D), wherein a content of the resin (A) contained in the resist composition is smaller than a content of the resin (B), (p-1)

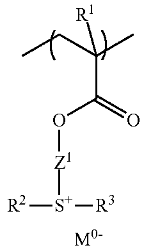

(p-2)

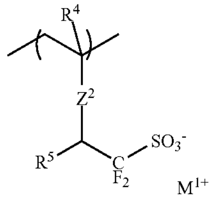

(a-1)

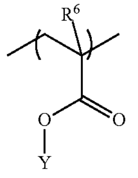

(b-1)

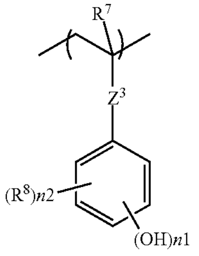

wherein in the general formula (p-1), $R^1$ represents a hydrogen atom or a methyl group;

$Z^1$ represents a single bond, a phenylene group, —O—$Z^{11}$—, —C(=O)—O—$Z^{11}$—, —C(=O)—NH—$Z^{11}$—, —$Z^{12}$-Ph-, —$Z^{12}$—O-Ph-, or —$Z^{12}$—C(=O)—O-Ph-; $Z^{11}$ represents an alkanediyl group having 1 to 6 carbon atoms, an alkenediyl group having 2 to 6 carbon atoms, or a phenylene group, $Z^{11}$ optionally having a carbonyl group, an ester bond, an ether bond, or a hydroxy group; $Z^{12}$ represents a hydrocarbon group having 1 to 15 carbon atoms; Ph represents a phenylene group;

$R^2$ and $R^3$ each independently represents a monovalent hydrocarbon group having 1 to 20 carbon atoms and optionally having a heteroatom, or a phenyl group;

$M^{0-}$ represents a non-nucleophilic counterion;

in the general formula (p-2), $R^4$ represents a hydrogen atom or a methyl group;

$Z^2$ represents a single bond, a phenylene group, —O—$Z^{21}$—, —C(═O)—O—$Z^{21}$—, —$Z^{21}$—C(═O)—O—, or —C(═O)—NH—$Z^{21}$—; $Z^{21}$ represents a single bond, an alkanediyl group having 1 to 20 carbon atoms, an alkenediyl group having 2 to 20 carbon atoms, or a phenylene group, $Z^{21}$ optionally having a carbonyl group, an ester bond, an ether bond, or a hydroxy group;

$M^{1+}$ represents a counter cation having a substituent and being a sulfonium cation, an iodonium cation, or an ammonium cation;

$R^5$ represents a hydrogen atom or a trifluoromethyl group;

in the general formula (a-1), $R^6$ represents a hydrogen atom or a methyl group;

Y represents a group having a structure changing in its polarity by an action of an acid to be soluble in an alkaline aqueous solution;

in the general formula (b-1), $R^7$ represents a hydrogen atom or a methyl group;

$Z^3$ represents a single bond, a methylene group, an ethylene group, a phenylene group, a fluorinated phenylene group, an ester bond, an amide bond, —O—$Z^{31}$—, —C(═O)—O—$Z^{31}$—, or —C(═O)—NH—$Z^{31}$—; $Z^{31}$ represents an alkanediyl group having 1 to 12 carbon atoms and optionally having a carbonyl group, an ester bond, or an ether bond;

"n1" represents an integer of 1 to 3; "n2" represents an integer of 0 to 3; a total of "n1" and "n2" is 5 or less; and $R^8$ represents a halogen atom, a linear hydrocarbon group having 1 to 10 carbon atoms, or a branched or cyclic hydrocarbon group having 3 to 10 carbon atoms, and —$CH_2$— constituting these groups are optionally substituted with —O—, —C(═O)—O—, or —C(═O)—, or optionally substituted with a hydrogen atom, a halogen atom, or a heteroatom.

2. The resist composition according to claim 1, wherein the non-nucleophilic counterion $M^{0-}$ in the general formula (p-1) is represented by the following general formula (e-0), (e-0)

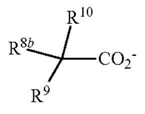

wherein $R^{8b}$ and $R^9$ each independently represent a hydrogen atom, a fluorine atom, or a trifluoromethyl group; and $R^{10}$ represents a hydrogen atom, a hydroxy group, a substituted or unsubstituted linear alkyl group having 1 to 20 carbon atoms, a substituted or unsubstituted branched or cyclic alkyl group having 3 to 20 carbon atoms, or a substituted or unsubstituted aryl group having 6 to 30 carbon atoms.

3. The resist composition according to claim 1, wherein the resin (A) and the resin (B) have no repeating unit having a lactone structure.

4. The resist composition according to claim 2, wherein the resin (A) and the resin (B) have no repeating unit having a lactone structure.

5. The resist composition according to claim 1, further comprising a resin (C) having no repeating unit changing in its polarity by an action of an acid to be soluble in an alkaline aqueous solution.

6. The resist composition according to claim 2, further comprising a resin (C) having no repeating unit changing in its polarity by an action of an acid to be soluble in an alkaline aqueous solution.

7. The resist composition according to claim 3, further comprising a resin (C) having no repeating unit changing in its polarity by an action of an acid to be soluble in an alkaline aqueous solution.

8. The resist composition according to claim 4, further comprising a resin (C) having no repeating unit changing in its polarity by an action of an acid to be soluble in an alkaline aqueous solution.

9. The resist composition according to claim 5, wherein the resin (C) has a repeating unit represented by the following general formula (c-1), (c-1)

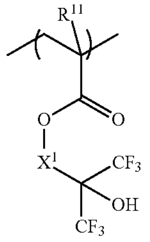

wherein $R^1$ represents a hydrogen atom or a methyl group; $X^1$ represents a single bond or a divalent linking group selected from a divalent hydrocarbon group having 1 to 10 carbon atoms, a fluorinated phenylene group, —O—$X^{11}$—, —C(═O)—O—$X^{11}$—, and —C(═O)—NH—$X^{11}$—; and $X^{11}$ represents an alkanediyl group having 1 to 20 carbon atoms and optionally having a carbonyl group, an ester bond, or an ether bond.

10. The resist composition according to claim 6, wherein the resin (C) has a repeating unit represented by the following general formula (c-1), (c-1)

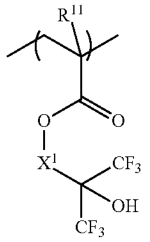

wherein $R^{11}$ represents a hydrogen atom or a methyl group; $X^1$ represents a single bond or a divalent linking group selected from a divalent hydrocarbon group having 1 to 10 carbon atoms, a fluorinated phenylene group, —O—$X^{11}$—, —C(═O)—O—$X^{11}$—, and —C(═O)—NH—$X^{11}$—; and $X^{11}$ represents an alkanediyl group having 1 to 20 carbon atoms and optionally having a carbonyl group, an ester bond, or an ether bond.

11. The resist composition according to claim 7, wherein the resin (C) has a repeating unit represented by the following general formula (c-1), (c-1)

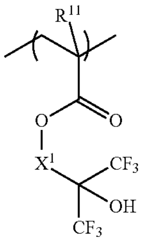

wherein $R^1$ represents a hydrogen atom or a methyl group; $X^1$ represents a single bond or a divalent linking group selected from a divalent hydrocarbon group having 1 to 10 carbon atoms, a fluorinated phenylene group, $—O—X^{11}—$, $—C(=O)—O—X^{11}—$, and $—C(=O)—NH—X^{11}—$; and $X^{11}$ represents an alkanediyl group having 1 to 20 carbon atoms and optionally having a carbonyl group, an ester bond, or an ether bond.

12. The resist composition according to claim 8, wherein the resin (C) has a repeating unit represented by the following general formula (c-1), (c-1)

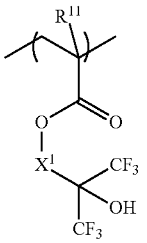

wherein $R^{11}$ represents a hydrogen atom or a methyl group; $X^1$ represents a single bond or a divalent linking group selected from a divalent hydrocarbon group having 1 to 10 carbon atoms, a fluorinated phenylene group, $—O—X^{11}—$, $—C(=O)—O—X^{11}—$, and $—C(=O)—NH—X^{11}—$; and $X^{11}$ represents an alkanediyl group having 1 to 20 carbon atoms and optionally having a carbonyl group, an ester bond, or an ether bond.

13. The resist composition according to claim 1, further comprising an onium salt (E) represented by the following general formula (e-1), (e-1)

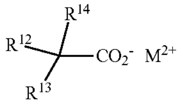

wherein $R^{12}$ and $R^{13}$ each independently represent a hydrogen atom, a fluorine atom, a hydrocarbon group having 1 to 10 carbon atoms and optionally having a fluorine atom, or a trifluoromethyl group;

$R^{14}$ represents a hydrogen atom, a hydroxy group, a substituted or unsubstituted linear alkyl group having 1 to 20 carbon atoms, a substituted or unsubstituted branched or cyclic alkyl group having 3 to 20 carbon atoms, the alkyl group optionally having an ether bond and an ester bond, or a substituted or unsubstituted aryl group having 6 to 30 carbon atoms; and $M^{2+}$ represents a counter cation having a substituent and being a sulfonium cation or an iodonium cation.

14. The resist composition according to claim 1, wherein the solvent (D) is a mixed solvent of two or three solvents selected from propylene glycol monomethyl ether acetate, propylene glycol dimethyl ether, ethyl lactate, γ-butyrolactone, and 4-hydroxy-4-methyl-2-pentanone.

15. A patterning process, comprising:

(i) a step of forming a resist film on a substrate by using the resist composition according to claim 1;

(ii) a step of exposing the resist film to KrF excimer laser with a wavelength of 248 nm, ArF excimer laser with a wavelength of 193 nm, EUV lithography with a wavelength of 13.5 nm, or electron beam; and (iii) a step of developing the exposed resist film with an alkaline developer.

* * * * *